US007790363B2

(12) United States Patent
Wonderling et al.

(10) Patent No.: US 7,790,363 B2
(45) Date of Patent: Sep. 7, 2010

(54) DIAGNOSTIC TEST FOR VITAMIN B$_{12}$

(75) Inventors: Ramani S. Wonderling, Ivanhoe, IL (US); John F. Uher, Kenosha, WI (US)

(73) Assignee: Abbott Laboratories Inc., Abbott Park, IL (US)

(*) Notice: Subject to any disclaimer, the term of this patent is extended or adjusted under 35 U.S.C. 154(b) by 176 days.

(21) Appl. No.: 11/052,128

(22) Filed: Feb. 7, 2005

(65) Prior Publication Data

US 2006/0177872 A1    Aug. 10, 2006

(51) Int. Cl.
*C12Q 1/00* (2006.01)
*G01N 33/53* (2006.01)
*G01N 35/00* (2006.01)
*G01N 33/566* (2006.01)
*G01N 33/567* (2006.01)

(52) U.S. Cl. .................. 435/4; 435/7.1; 436/43; 436/501; 436/505

(58) Field of Classification Search .................. None
See application file for complete search history.

(56) References Cited

U.S. PATENT DOCUMENTS

| | | | |
|---|---|---|---|
| 3,591,678 | A | 7/1971 | Ellenbogen, et al. |
| 4,447,528 | A | 5/1984 | Ellis et al. |
| 4,582,788 | A | 4/1986 | Erlich et al. |
| 4,683,194 | A | 7/1987 | Saiki et al. |
| 4,683,202 | A | 7/1987 | Mullis |
| 4,945,050 | A | 7/1990 | Sanford et al. |
| 5,227,311 | A | 7/1993 | Kuemmerle et al. |
| 5,231,020 | A | 7/1993 | Jorgensen et al. |
| 5,350,674 | A | 9/1994 | Boenisch et al. |
| 5,459,242 | A | 10/1995 | Kuemmerle |
| 5,795,784 | A | 8/1998 | Arnquist et al. |
| 5,912,120 | A | 6/1999 | Goldstein et al. |
| 6,183,723 | B1 | 2/2001 | Seetharam et al. |

FOREIGN PATENT DOCUMENTS

| | | |
|---|---|---|
| EP | 0 050 424 | 4/1982 |
| EP | 0 084 796 | 8/1983 |
| EP | 0 201 184 | 12/1986 |
| EP | 0 237 362 | 9/1987 |
| EP | 0 258 017 | 3/1988 |
| JP | 05-015375 | 1/1993 |
| JP | 05-049478 | 3/1993 |
| JP | 06-153935 | 6/1994 |
| JP | 06-205673 | 7/1994 |
| WO | 92/18539 | 10/1992 |
| WO | WO00/71754 | 11/2000 |
| WO | WO03/006661 | 1/2003 |

OTHER PUBLICATIONS

Kuemmerle et al., Automated Assay of Vitamin 6-12 by the Abbott Imx Analyzer, Clin. Chem., 1992, 38/10, 2073-2077.*
Ngo et al., in The Protein Folding Problem and Tertiary Structure Prediction, 1994, Merz et al. (ed.), Birkhauser, Boston, MA, pp. 433 and 492-495.*
Ausubel, et al., Techniques in Biochemistry and Molecular Biology-Hybridization with Nucleic Acid Probes, "Overview of principles of hybridization and the strategy of nucleic acid assays", Short Protocols in Molecular Biology, 19-78, (1993).
Turner, et al., The Potential Exploitation of Plant Viral Translational Enhancers in Biotechnology for Increased Gene Expression, *Molecular Biotechnology*, 3:225-236 (1995).
Ingelbrecht, et al., Different 3' End Regions Strongly Influence the Level of Gene Expression in Plant Cells, The Plant Cell 1:671-680 (1989).
Klein, et al., High-velocity microprojectiles for delivering nucleic acids into living cells, Nature (London) 327:70-73 (1987).
Jones, et al., High level expression of introduced chimaeric genes in regenerated transformed plants, The EMBO Journal, vol. 4, No. 10, 2411-2418 (1985).
De Almeida, et al., Transgenic expression of two marker genes under the control of an *Arabidopsis rbcS* promoter: Sequences encoding the Rubisco transit peptide increase expression levels., Mol. Gen. Genetics, 218: 78-86 (1989).
Mullis, et al., Specific Enzymatic Amplification of DNA In Vitro: The Polymerase Chain Reaction, Cold Spring Harbor Symposia on Quantitative Biology, vol. LL: 263-273 (1986).
Ishida, et al., High efficiency transformation of maize (Zea *mays* L.) mediated by *Agrobacterium tumefaciens*, Nature Biotechnology, vol. 14: 745-750 (Jun. 1996).
Abbott Laboratories, Abbott AxSym® System B12 (Feb. 1999) Abbott Park, Illinois.
Abbott Laboratories, Architect™ System B12 (Dec. 1998) Abbott Park, Illinois.
Abbott Laboratories, IM® X System B12 (1999) Abbott Park, Illinois.
Hoogenboom, Designing and optimizing library selection strategies for generating high-affinity antibodies, TIBTECH, vol. 15: 62-70 (1997).
Kellermann, et al., Antibody discovery: the use of transgenic mice to generate human monoclonal antibodies for therapeutics, Current Opinion in Biotechnology, vol. 13: 593-597 (2002).
Gavilondo, et al., Antibody Engineering at the Millennium, BioTechniques, vol. 29, No. 1: 128-145 (2000).
Azzazy, et al, Phage display technology: clinical applications and recent innovations, Clinical Biochemistry, vol. 35: 425-445 (2002).

(Continued)

*Primary Examiner*—Suzanne M Noakes
*Assistant Examiner*—Jae W Lee
(74) *Attorney, Agent, or Firm*—David L. Weinstein

(57) ABSTRACT

An isolated nucleotide sequence or fragment thereof encoding the porcine intrinsic factor, wherein the porcine intrinsic factor comprises an amino acid sequence having at least 85% amino acid sequence identity to an amino acid sequence selected from the group consisting of SEQ ID NO: 3, SEQ ID NO: 6, and SEQ ID NO: 9. The invention also encompasses an isolated nucleic acid sequence or fragment thereof comprising, or complementary to, a nucleotide sequence having at least 85% nucleotide sequence identity to a nucleotide sequence selected from the group consisting of SEQ ID NO: 1, SEQ ID NO: 4, and SEQ ID NO: 7. The porcine intrinsic factor can be use is an assay to determine the quantity of vitamin B$_{12}$ in a biological sample.

4 Claims, 9 Drawing Sheets

OTHER PUBLICATIONS

Taylor, et al., A transgenic mouse that expresses a diversity of human sequence heavy and light chain immunoglobins, Nucleic Acids Research, vol. 20, No. 23: 6287-6295 (1992).

Ward, et al., Binding activities of a repertoire of single immunoglobin variable domains secreted from *Escherichia coli*, Nature, vol. 341: 544-546 (1989).

Poljak, Production and structure of diabodies, Structure, vol. 2, No. 12: 1121-1123 (1994).

Kipriyanov, et al., Single-chain antibody streptavidin fusions: Tetrameric bifunctional scFv-complexes with biotin binding activity and enhanced affinity to antigen, Human Antibodies and Hybridomas, vol. 6, No. 3: 93-101 (1995).

Giege, et al., An introduction to the crystallogenesis of biological macromolecules, Crystallization of Nucleic Acids and Proteins a Practical Approach, $2^{nd}$ edition, 1-20 (1999).

Kipriyanov, et al., Recombinant Single-Chain Fv Fragments Carrying C-Terminal Cysteine Residues: Production of Bivalent and Biotinylated Miniantibodies, Molecular Immunology, vol. 31, No. 14: 1047-1058 (1994).

Bird, et al., Single—Chain Antigen—Binding Proteins, Science, vol. 242: 423-426 (1988).

Little, et al., Of mice and men: hybridoma and recombinant antibodies, Immunology Today, vol. 21, No. 8: 364-370 (2000).

Hoogenboom, et al., Natural and designer binding sites made by phage display technology, Immunology Today, vol. 21, No. 8: 371-378 (2000).

Huston, et al., Protein engineering of antibody binding sites: Recovery of specific activity in an anti-digoxin single-chain Fv analogue produced in *Eschericha coli*, Proc. Natl. Acad. Sci., vol. 85: 5879-5883 (1988).

Holliger, et al., "Diabodies": Small bivalent and bispecific antibody fragments, Proc. Natl. Acad. Sci., vol. 90: 6444-6448 (1993).

Center for Animal Functional Genomics, "Generation of ESTs from mixed pig cDNA libraries", Accession No. CA780388 (2002).

Hansen, et al, "Gene Expression Profiling of the Bovine Gastrointestinal Tract", Accession No. CB220029 (2002).

\* cited by examiner

Binding of recombinant porcine Intrinsic Factor to B12

Expression of Porcine Intrinsic Factor in
pET32a Rosettagami B DE3 and pET32a BL21 DE3 *E.coli*

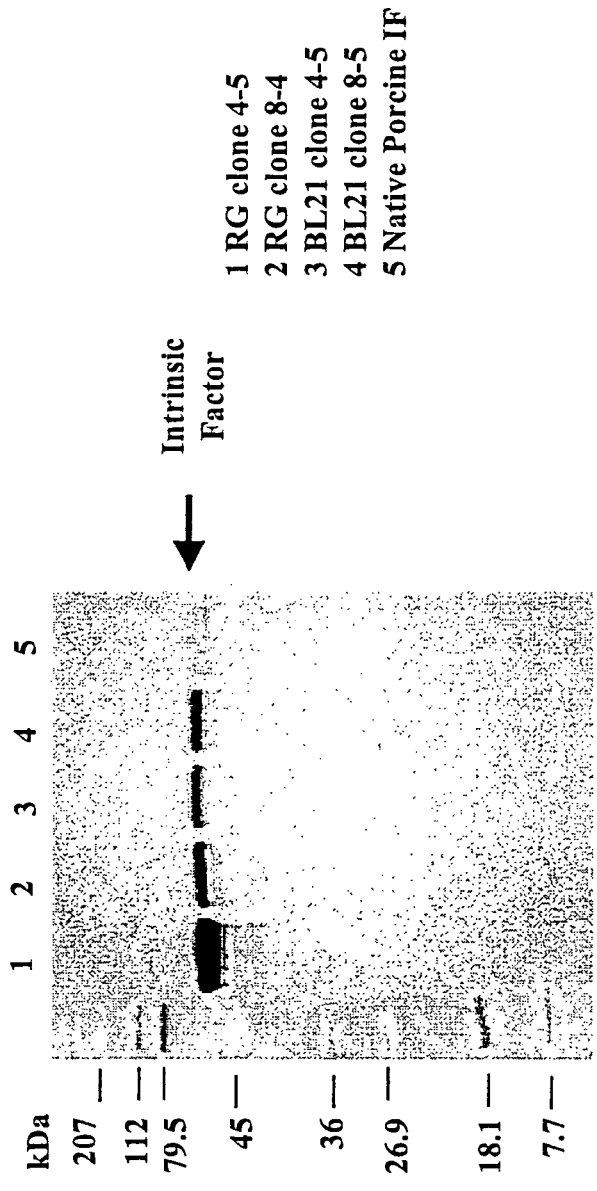

Alignment Report of Untitled ClustalW (Slow/Accurate, IUB)
Friday, February 04, 2005 10:07 AM

FIG. 4 (1 of 3)

Alignment Report of Untitled ClustalW (Slow/Accurate, IUB)
Friday, February 04, 2005 10:07 AM

```
        TCCTGTGGGTTCTGAGGAAGGCTACAGAGCCCTGTTTGGTCAGGTACTGAAGGATATTGTGGAGAATATCAGCTTGAGGA Majority
              570       580       590       600       610       620       630       640
561     TCCTGTGGGTTCTCAAGAAAACTACAGAGACCTGTTTCGTCAGGCACTGAAGGCTATTGTGGAGAAGATCAGCTTAAGGA Mouse IF
561     TCCTGTGGGTTCTCAGGAAAACTACAGAGACCTGTTTCGTCAGGCACTGAAGGTTATTGTGGATAATATCAGCTTGAGGA Rat IF
561     CCCTGTAGGCTCAGAGGAAGGTTACAGATCCCTGTTTCGTCAGGTACTAAAGCATATTGTGGAGAAAATCAGCATGAAGA Human IF
547     CCCCGTAGGCTCAGAGGAAGGGTACAGAGCCCTGTTCAGTCAGGTACTGAGGAATACTGTGGAGAATATCAGCATGAGGA Porcine IF TCAAAGCTGATGGCATCATTGGAGACATCTACAGCACTGGCCTTGCCATGCAGGCTCTCTCTGTGACACCTGAGCAACCT Majority
              650       660       670       680       690       700       710       720
641     TCAAAGCTGATGGCATCATCGGAGACATCTACAGCACTGGCCTTGCCATGCAGGCTCTCTCGTGACACCTGAGCAACCT Mouse IF
641     TCAAAGCTGATGGTATTATTGGAGACATCTACAGCACTGGCCTTGCCATGCAGGCTCTCTCTGTGACACCTGAGCAACCT Rat IF
641     TCAAAGATAATGGGATCATTGGACACATCTACAGTACTGGCCTCGCCATGCAGGCTCTCTCTGTAACACCTGAGCCATCT Human IF
627     TCCAAGACAACGGAATCATTGGAAACATCTATAGCACTGGCCTCGCCATGCAGGCTCTCTCTGTGACACCTGAGCAACCT Porcine IF ACCAAGGAGTGGGACTGTGAGAAGACTATGGATACGATACTCAATGAGATTAAGCAGGGGAAATTCCACAACCCCATGTC Majority
              730       740       750       760       770       780       790       800
721     ACCAAGAAGTGGGACTGTGAGAAGACTATGCATACAATACTCAAGGAGATTAAGCAAGGGAAATTCCAAAACCCCATGTC Mouse IF
721     ACCAAAGAGTGGGACTGTGAGAAGACTATGTATACGATACTCAAGGAGATTAAGCAGGGGAAATTCCACAACCCCATGTC Rat IF
721     AAAAAGGAATGGAACTGCAAGAAGACTACGGATATGATACTCAATGAGATTAAGCAGGGGAAATTCCACAACCCCATGTC Human IF
707     AACAAGGAGTGGGACTGCCAGAAGACCATGGATACTGTACTTACTGAGATTAAGGAGGGGAAATTCCACAACCCCATGGC Porcine IF CATTGCCCAAATTCTCCCTTCCTTGAAAGGCAAGCTTACCTAGATGTGCCCCAAGTAACTTGTGGTCCTGATCATGAGG Majority
              810       820       830       840       850       860       870       880
801     CATTGCCCAAATTCTCCCTTCCTTGAAAGGCAAGACTTACCTAGATGTGCCCCAACTAAACATGTGGCCTGATCATGAAG Mouse IF
801     CATTGCCCACATTCTCCCTTCCTTGAAAGGCAAGACTTACCTAGATGTGCCCCAAGTAACGTGTGGCCCTGATCATGAAG Rat IF
801     CATTGCCCAAATCCTCCCTTCCCTGAAAGGCAAGACATACCTAGATGTGCCCCACGTCACTTGCAGCCTGATCATGAGG Human IF
787     CATTGCCCAAATCCTCCCTTCCCTGAAAGGCAAGACCTATCTAGATGTGCCCCATGTGCTTGCAGCCCTGGTCATGAGG Porcine IF TGCCACCAACTTTACCTGACTATCCTAGCCCTGTCCCCACTTCAGTATCTAACATCACCGTCATATACACCATAAATAAC Majority
              890       900       910       920       930       940       950       960
881     TGCCACCAACTTTAACTGACTATCCTACCCCGGTCCCCACTTCAGTATCTAACATTACCGTCATATATACCATAAACAAC Mouse IF
881     TGCCACCAACTTTTAACTGACTATCCTACCCCGGTCCCCACTTCAATATCTAATATCACGGTCATATACACCATAAACAAC Rat IF
881     TACAACCAACTCTACCCAGCAACCCTGGCCCTGCCCCCACCTCTGCATCTAACATCACTGTCATATACACCATAAATAAC Human IF
867     TGCCACCAACTCTACCCAACCACCCCAGCCCTGTTCCCACCCCAGCACCCAACATCACCGTCATATACACCATAAATAAC Porcine IF CAGCTGAGGGGGGTTGATCTGCTTTTCAATGTGACCATCGATGTTAGTGTGAAAAGTGGATCTGTGCTACTTGTTGTCCT Majority
              970       980       990      1000      1010      1020      1030      1040
961     CAGCTGAGAGGCGGTTGATCGGCTTTTCAATGTCACCATCGACGTTAGTGTGAAAAGTGGATCTGTGCTACTTGCTGTCCT Mouse IF
961     CAGCTGAGGGGCGGTTGATCTGCTTTTCAATGTCACCATCGACGTTAGTGTGAAAAGTGGATCTGTGCTCCTTGCTGTCCT Rat IF
961     CAGCTGAGGGGCGGTTGAGCTGCTCTTCAACGAGACCATCAATGTTAGTGTGAAAAGTGGGTCAGTGTACTTGTTGTCCT Human IF
947     CAGCTGAGGGGCGTGGAGCTGCTCTTCAATGAAACCATCAGTGTTAGTGTGAAAAGAGGATCCGTGCTACTTATTGTCCT Porcine IF GGAGGAAGCACAGCGCAAAAACCCCATGTTCAAATTTGAAACCACAATGACATCCTGGGGCCTTGTTGTCTCTTCTATCA Majority
              1050      1060      1070      1080      1090      1100      1110      1120
1041    GGAAGAAGCACAGCGCAAAAACTCCATGTTCAAATTTGAAACCACAATGACATCCTGGGGCCTTATTGTCTCTTCTATCA Mouse IF
1041    GGAAGAAGCCCAGCGCACAAACCCATGTTCAAATTTGAAACCACAATGACATCCTGGGGCCTTATTGTCTCTTCTATCA Rat IF
1041    AGAGGAAGCACAGCGCAAAAATCCTATGTTCAAATTTGAAACCACAATGACATCTGGGGCCTTGTCGTCTCTTCTATCA Human IF
1027    GGAGGAGGCACAGCGCAAAAACCCCAAGTTCAAATTTGAAACGACAATGACGTCCTGGGGACCGGTGGTCTCTTCTATTA Porcine IF
```

Alignment Report of Untitled ClustalW (Slow/Accurate, IUB)
Friday, February 04, 2005 10:07 AM

```
         ACAATATCGCTGAGAATGTTAATCACAAGACATACTGGGAGTTTCTTAGTGGCAAAACGCCTTTGGATGAAGGGGTTGCT Majority
                1130      1140      1150      1160      1170      1180      1190      1200
1121 ACAATATCGCTGAGAATGTTAATCACAAGACATACTGGGAGTTTCTTAGTGGCAAAACGCCTTTGCATGAAGGGGTTGCT Mouse IF
1121 ACAATATCGCTGAGAATGTTAAGCACAAGACCTATTGGCAGTTCCTTAGTGGCAAAACGCCTTTGGGTGAAGGGGTTGCA Rat IF
1121 ACAATATCGCGGAAAATGTTAATCACAAGACATACTGGCAGTTTCTTAGTGGTGTAACACCTTTGAATGAAGGGGTTGCT Human IF
1107 ACAATATCGCTGAAAATGTCAACCACAGGACGTACTGGCAGTTTCTGAGTGGCCAAACGCCCTTAAACGAAGGAGTTGCG Porcine IF TACTATATACCCTTCAACCACGAGCACATCACAGCCAATTTCACCCAGTACTGA                         Majority
                1210      1220      1230      1240      1250
1201 TACTATATCCCCTTCAATCATGAGCACATCACAGCCAACTTCACCCAATACTGA                          Mouse IF
1201 TACTATATTCCCTTCAACTACGAGCACATCACAGCCAACTTCACCCAATACTGA                          Rat IF
1201 GACTAGATACCCTTCAACCACGAGCACATCACAGCCAATTTCACACAGTACTAA                          Human IF
1187 GACTATATACCCTTCAACCACGAGCACATCACAGCCAATTTCACACAG                                Porcine IF
```

Decoration 'Decoration #1': Shade (with solid black) residues that differ from Porcine IF.

FIG. 4 (3 of 3)

Sequence pair distances of Untitled ClustalW (Slow/Accurate, IUB)
Friday, February 04, 2005 10:08 AM Percent Identity

| | | 1 | 2 | 3 | 4 | | |
|---|---|---|---|---|---|---|---|
| Divergence | 1 | ■ | 92.4 | 82.9 | 78.8 | 1 | Mouse IF |
| | 2 | 8.1 | ■ | 82.4 | 78.5 | 2 | Rat IF |
| | 3 | 19.8 | 20.4 | ■ | 83.3 | 3 | Human IF |
| | 4 | 23.6 | 24.0 | 17.4 | ■ | 4 | Porcine IF |
| | | 1 | 2 | 3 | 4 | | |

FIG. 5

Alignment Report of Untitled ClustalW (Slow/Accurate, Gonnet)
Monday, January 31, 2005 2:07 PM

```
     ----MAWLXLYLLSVLWAVAGTSTQAQSSCSVPSAQQPLVNGLQVLMENSVTSSAFPNPSILIAMNLAGAYNLEAQKLLT Majority
             10        20        30        40        50        60        70        80

1  MWKGMAWLSFYLLNVLWAVAGTSTRAQRSCSVPPDQQEWVNGLQLLMENSVTESDLPNPSILIAMNLASTYNLEAQKLLT Rat IF
  1  ----MAWLTLYLLSVLWAVAGTSTRAQSSCSVPPDQQEWVDGLQALMENSVTESDFPNPSILIAMNLAGAYNLEAQKLLT Mouse IF
  1  ----MAWFALYLLSLLWATAGTSTQTQSSCSVPSAQEPLVNGIQVLMENSVTSSAYPNPSILIAMNLAGAYNLKAQKLLT Human IF
  1  --------LYLLSLLWAVAGTSTQTRSSCSVPSAEQPLVNGIQVLMEQSVTSSAFPNPSILIAMNLAGAYNTEAQELLT Porcine IF YQLMASDSADLTXGQLALTIMALTSSCRDPGSKVSILQKQMENWAPSSLGAEASAFYGPSLAILALCQKNSEATLPIAVR Majority
             90       100       110       120       130       140       150       160

81  YQLMASDSADLTNGQLALTIMALTSSCRDPGSKVSILQKNMESWIPSNIGAESSSFYGPALAILALCQKNSEATLPIAVR Rat IF
 77  YQLMASDSANLTSGQLALTVMALTSSCRDPGSKVSTLLKKMENWSPSSPGAESSAFYGPCLAILALCQKSSEATLPIAVA Mouse IF
 77  YQLMSSDNNDLTIGHLGLTIMALTSSCRDPGDKVSILQRQMENWAPSSPNAEASAFYGPSLAILALCQKNSEATLPIAVR Human IF
 72  YKLMATNTSDLTTGQLALTIMALTSSCRDPGNRIAILQGQMENWAPPSLDTHASTFYEPSLGILTLCQNNPEKTLPLAAR Porcine IF FAKTLLAESSPFNVDTGAVATLALTCMYNKIPVGSEEGYRDLFGQALKXIVENISLRIKADGIIGDIYSTGLAMQALSVT Majority
            170       180       190       200       210       220       230       240

161  FAKTIMMESSPFSVDTGAVATLALTCMYNRIPVGSQENYRDLFGQALKVIVLNISLRIKADGIIGDIYSTGLAMQALSVT Rat IF
157  FAKTLMMEPSPFNVDTGAVATLALTCMYNKIPVGSQENYRDLFGQALKAIVEKISLRIKADGIIGDIYSTGLAMQALSVT Mouse IF
157  FAKTLLANSSPFNVDTGAMATLALTCMYNKIPVGSEEGYRSLFGQVLKDIVEKISMKIKDNGIIGDIYSTGLAMQALSVT Human IF
152  FAKTLLANSSPFNMDTGAMATLALTCMYNKIPVGSEEGYRALFSQVLRNTVENISMRIQDNGIIGNIYSTGLAMQALSVT Porcine IF PEQPTKEWDCEKTMDTILNEIKQGKFQNPMSIAQILPSLKGKTYLDVPQVTCGPDHEVPPTLTDYPTPVPTSASNITVIY Majority
            250       260       270       280       290       300       310       320

241  PEQPTKEWDCEKTMTILNEIKQGKFQNPMSIAQILPSLKGKTYLDVPQVICGPDHEVPPTLTDYPIPVPTSISNITVIY Rat IF
237  PEQPTKKWDCEKTMHTLLNEIKQGKFQNPMSIAQILPSLKGKTYLDVPQVICGPDHEVPPTLTDYPLPVPTSVSNITVIY Mouse IF
237  PEPSKKEWNCKKTIDMILNEIKQGKFHNPMSIAQILPSLKGKTYLDVPQVICSFDHEVQPTLFSNPGPTSASNITVIY Human IF
232  PEQPNKEWDCQKTMDTVLTEIKEGKFHNPMAIAQILPSLKGKTYLDVPHVSCSPGHEVPPTLPNHPSPVPTPAPNITVIY Porcine IF TINNQLRGVDLLFNVTIEVSVKSGSVLLAVLEEAQRKNPMFKFETTMTSWGLVVSSINNIAENVNHKTYWEFLSGKTPLN Majority
            330       340       350       360       370       380       390       400

321  TINNQLRGVDLLFNVTIEVSVKSGSVLLAVLEEAQRRNHMFKFETTMTSWGLIVSSINNIAENVKHKTYWEFLSGKTPLG Rat IF
317  TINNQLRGVDELFNVTIEVSVKSGSVLLAVLEEAQRKNSMFKFETTMTSWGLIVSSINNIAENVNHKTYWEFLSGKTPID Mouse IF
317  TINNQLRGVELLFNETIEVSVKSGSVLLVVLEEAQRKNPYFKFETTMTSWGLVVSSINNIAENVNHKTYWQFLSGVTPLN Human IF
312  TINNQLRGVELLFNETISVSVKRGSVLLIVLEEAQRKNPKFKFETTMTSWGPVVSSINNIAENVNHRTYWQFLSGQTPLN Porcine IF EGVADYIPFNHEHITANFTQY                                                          Majority
            410       420

401  EGVANYIPFNMEHITANFTQY                                                          Rat IF
397  EGVAYYIPFNHEHITANFTQY                                                          Mouse IF
397  EGVADYIPFNHEHITANFTQY                                                          Human IF
392  EGVADYIPFNHEHITANFTQY                                                          Porcine IF
```

Decoration 'Decoration #1': Shade (with solid black) residues that differ from Porcine IF.

FIG. 6

Sequence pair distances of Untitled ClustalW (Slow/Accurate, Gonnet)
Monday, January 31, 2005 2:08 PM Percent Identity

|  | 1 | 2 | 3 | 4 |  |  |
|---|---|---|---|---|---|---|
| 1 |  | 89.3 | 78.6 | 72.2 | 1 | Rat IF |
| 2 | 10.6 |  | 80.8 | 73.4 | 2 | Mouse IF |
| 3 | 24.2 | 22.2 |  | 80.8 | 3 | Human IF |
| 4 | 32.3 | 31.5 | 20.9 |  | 4 | Porcine IF |
|  | 1 | 2 | 3 | 4 |  |  |

Divergence

FIG. 7

DIAGNOSTIC TEST FOR VITAMIN B$_{12}$

BACKGROUND OF THE INVENTION

1. Field of the Invention

This invention relates to reagents for diagnostic testing, and more particularly, reagents for diagnostic testing carried out by automated immunoassay analyzers.

2. Discussion of the Art

Anemia is the major disorder related to low serum vitamin B$_{12}$ levels. Megaloblastic anemia (MA), characterized by elevated mean corpuscular volume (MCV), has been found to be due to vitamin B$_{12}$ deficiency. The relationship between vitamin B$_{12}$ levels and MA is not always clear in that some patients with MA will have normal vitamin B$_{12}$ levels; conversely, many individuals with vitamin B$_{12}$ deficiency are not afflicted with MA. Despite these complications, however, in the presence of MA (e.g., elevated MCV) there is usually serum vitamin B$_{12}$ deficiency. A major cause of vitamin B$_{12}$ deficiency is pernicious anemia. This disease is characterized by poor vitamin B$_{12}$ uptake, resulting in below normal serum vitamin B$_{12}$.

There a number of conditions that manifest themselves as low serum vitamin B$_{12}$ levels, including iron deficiency, normal near-term pregnancy, vegetarianism, partial gastrectomy/ileal damage, oral contraception, parasitic competition, pancreatic deficiency, treated epilepsy, and advancing age. Disorders associated with elevated serum vitamin B$_{12}$ levels include renal failure, liver disease, and myeloproliferative diseases.

Intrinsic factor binds vitamin B$_{12}$. This characteristic enables the detection of and measurement of the quantity of vitamin B$_{12}$ in biological samples. In conventional preparation of intrinsic factor, the intrinsic factor protein is isolated from porcine tissue by means of an expensive, tedious, and time-consuming process.

cDNA cloning using reverse transcriptase-polymerase chain reaction technique (RT-PCR) is well-known in the art. The designing of primers based on homology known for this particular protein in other species (such as human, mouse and rat) and selecting the appropriate PCR conditions to obtain cDNA require a significant amount of planning and expertise in the PCR-based cloning technique.

U.S. Pat. No. 3,591,678 discloses a process for purifying intrinsic factor by a batch chromatography process that utilizes an ion exchange resin. Impure intrinsic factor is dissolved in a buffer solution having relatively low pH and ionic strength, and the resultant solution is contacted with a cellulosic exchange resin. The resin is separated from the solution and the purified intrinsic factor is eluted therefrom with a buffer solution having a higher pH and ionic strength than the buffer solution in which the impure intrinsic factor was dissolved.

U.S. Pat. No. 4,447,528 discloses a radioassay procedure and reagent kit therefore for detecting auto-blocking antibody, such as auto blocking antibody which interferes with the complexation of intrinsic factor with vitamin B$_{12}$. A receptor, i.e., intrinsic factor, is immobilized on a support and the amount of ligand, i.e., vitamin B$_{12}$, capable of binding therewith in the presence of a biological fluid sample is determined.

U.S. Pat. Nos. 5,227,311 and 5,459,242 disclose a method for purifying an aqueous intrinsic factor solution which contains R-protein. The method involves adding to the intrinsic factor solution an amount of colloidal silica to disperse lipid emulsion, an amount of cobinamide sufficient to bind substantially all of the R-protein in the solution and an amount of an intrinsic factor affinity resin sufficient to bind the intrinsic factor in the solution, washing the bound cobinamide and the R-protein from the resin, eluting the intrinsic factor from the resin, and dialyzing the eluted intrinsic factor. Also disclosed is a kit for conducting an assay for cobalamins which includes a conjugate of microparticles and purified intrinsic factor.

U.S. Pat. No. 5,350,674 discloses a non-isotopic competitive assay for vitamin B$_{12}$, utilizing intrinsic factor labeled with horseradish peroxidase, by coupling via heterobifunctional cross-linking agents. In addition, a method for stabilizing the resultant conjugates by pretreatment with N-ethylmaleimide is disclosed.

Prior investigators have disclosed the cDNA sequences encoding human intrinsic factor (Genbank Accession No. M63154), mouse intrinsic factor (Genbank Accession No. L24191) and rat intrinsic factor (Genbank Accession No. J03577). However, the cDNA sequence of the porcine intrinsic factor is not known. Therefore, prior to this invention, recombinant porcine intrinsic factor protein could not be produced.

Porcine intrinsic factor is typically isolated from the tissue of the duodenum of a hog (e.g., *Sus scrofa*). This isolation is a tedious, expensive, and time-consuming procedure, and the yields are low. The native intrinsic factor isolated by currently used procedures lacks consistency in its purity and in its resulting performance in an immunoassay. Therefore, it would be desirable to produce porcine intrinsic factor in large quantities and to isolate porcine intrinsic factor in a single-step affinity isolation process. Recombinant protein produced in this manner would have consistent performance in a diagnostic immunoassay.

SUMMARY OF THE INVENTION

The present invention includes an isolated nucleotide sequence or fragment thereof encoding porcine intrinsic factor, wherein the porcine intrinsic factor comprises an amino acid sequence having at least 85% amino acid sequence identity to an amino acid sequence selected from the group consisting of SEQ ID NO: 3, SEQ ID NO: 6, and SEQ ID NO: 9.

Additionally, the present invention encompasses an isolated nucleic acid sequence or fragment thereof comprising, or complementary to, a nucleotide sequence having at least 85% nucleotide sequence identity to a nucleotide sequence selected from the group consisting of SEQ ID NO: 1, SEQ ID NO: 4, and SEQ ID NO: 7.

The nucleotide sequences described above encode a functionally active porcine intrinsic factor that binds vitamin B$_{12}$. The present invention also includes purified proteins and fragments thereof encoded by the above-referenced nucleotide sequences.

Additionally, the present invention includes a method of producing porcine intrinsic factor comprising the steps of: isolating a nucleotide sequence comprising or complementary to a nucleotide sequence encoding a porcine intrinsic factor an amino acid sequence having at least 85% identity to an amino acid sequence of SEQ ID NO: 3, SEQ ID NO: 6, and SEQ ID NO: 9; constructing a vector comprising: i) the isolated nucleotide sequence operably linked to ii) a promoter; and introducing said vector into a host cell for a time and under conditions sufficient for expression of the porcine intrinsic factor. The host cell may be, for example, a eukaryotic cell or a prokaryotic cell. In particular, the prokaryotic cell may be, for example, *E. coli*, cyanobacteria or *B. subtilis*. The eukaryotic cell may be, for example, a mammalian cell, an insect cell, a plant cell or a fungal cell (e.g., a yeast cell such as *Saccharomyces cerevisiae*, *Saccharomyces carlsber-*

*gensis, Candida* spp., *Lipomyces starkey, Yarrowia lipolytica, Kluyveromyces* spp., *Hansenula* spp., *Trichoderma* spp. or *Pichia* spp.). Other fungal hosts such as *Rizopus* spp., *Aspergillus* spp. and *Mucor* spp. may also be utilized.

Moreover, the present invention also includes a vector comprising: an isolated nucleotide sequence comprising or complementary to a nucleotide sequence encoding the porcine intrinsic factor having an amino acid sequence having at least 85% amino acid identity to an amino acid sequence selected from the group consisting of SEQ ID NO: 3, SEQ ID NO: 6, and SEQ ID NO: 9, operably linked to a regulatory sequence (e.g., a promoter). The invention also includes a host cell comprising this vector. The host cell may be, for example, a eukaryotic cell or a prokaryotic cell. Suitable eukaryotic cells and prokaryotic cells are as defined above.

Additionally, the present invention includes an isolated nucleic acid sequence or fragment thereof which hybridizes, under moderate or high stringency conditions, to a nucleic acid sequence selected from the group consisting of SEQ ID NO: 1, SEQ ID NO: 4, and SEQ ID NO: 7.

The present invention also encompasses an isolated nucleic acid or fragment thereof, which hybridizes, under moderate or high stringency conditions, to an isolated nucleic acid sequence encoding porcine intrinsic factor, wherein the amino acid sequence of the porcine intrinsic factor has at least 85% identity to an amino acid sequence selected from the group consisting of SEQ ID NO: 3, SEQ ID NO: 6, and SEQ ID NO: 9.

It should be noted that the present invention also encompasses isolated nucleotide sequences (and the corresponding encoded proteins) having sequences comprising, corresponding to, identical to, or complementary to at least about 70%, preferably at least about 80%, and more preferably at least about 85% identity to SEQ ID NO: 1, SEQ ID NO: 4, and SEQ ID NO: 7. (All integers (and portions thereof) between 70% and 100% are also considered to be within the scope of the present invention with respect to percent identity.) Such sequences may be derived from any source, either isolated from a natural source, or produced via a semi-synthetic route, or synthesized de novo. In particular, such sequences may be isolated or derived from sources other than described in the examples (e.g., bacteria, fungus, algae, *C. elegans*, mouse or human).

Furthermore, the present invention also encompasses fragments and derivatives of the nucleic acid sequences of the present invention (i.e., SEQ ID NO: 1, SEQ ID NO: 4, and SEQ ID NO: 7), as well as of the sequences derived from other sources, and having the above-described complementarity, identity or correspondence. Functional equivalents of the above full length sequences and fragments are also encompassed by the present invention.

The method of this invention involves cloning the cDNA encoding porcine intrinsic factor by RT-PCR (Reverse Transcriptase-Polymerase Chain Reaction). The design of the primers was based on the homology that exists between the intrinsic factor cDNA sequences of human, mouse, and rat.

Intrinsic factor isolated by methods currently used in the art provides an inconsistent result with respect to purity, and, consequently, performance in an assay. By employing the method and protein of this invention, recombinant intrinsic factor having consistent properties can be produced. The method of this invention reduces cost and simplifies isolation. Furthermore, the results of the assays using porcine intrinsic factor show improved consistency.

BRIEF DESCRIPTION OF THE DRAWINGS

FIG. 3 illustrates the binding of recombinant porcine intrinsic factor to anti-intrinsic factor antibody by Western blotting. The *E. coli* cells were lysed and the proteins were resolved using SDS-PAGE and blotted onto a nitrocellulose membrane. The membrane was then probed with anti-intrinsic factor antibody. Lane 1 contains molecular weight markers (marked in kilodaltons). Lanes 2, 3, 4, and 5 represent cells from various clones expressing recombinant porcine intrinsic factor. Lane 6 contains the native porcine intrinsic factor (purified from hog (*Sus scrofa*) gut). The recombinant intrinsic factor protein band developed color, thereby demonstrating that the recombinant intrinsic factor was recognized by the antibody.

FIG. 4 illustrates the alignment of the nucleotide sequences of porcine intrinsic factor, human intrinsic factor, rat intrinsic factor, and mouse intrinsic factor. SEQ ID NO: 18 represents the nucleotide sequence of the human IF $DNA_{1-1254}$ (1254 bp). SEQ ID NO: 19 represents the nucleotide sequence of the mouse IF $DNA_{1-1254}$ (1254 bp). SEQ ID NO: 20 represents the nucleotide sequence of the rat IF $DNA_{1-1254}$ (1254 bp). SEQ ID NO: 21 represents the nucleotide sequence of the porcine IF $DNA_{14-1248}$ (1234 bp). SEQ ID NO: 22 represents the nucleotide sequence of the majority IF $DNA_{1-1254}$ (1254 bp).

FIG. 5 illustrates the percent identity between the nucleotide sequences of porcine intrinsic factor and human intrinsic factor, between the nucleotide sequences of porcine intrinsic factor and rat intrinsic factor, and between the nucleotide sequences of porcine intrinsic factor and mouse intrinsic factor.

FIG. 6 illustrates the alignment of the putative amino acid sequence of intrinsic factor coded by *Sus scrofa* with known intrinsic factor sequences from human, rat, and mouse. SEQ ID NO: 23 represents the amino acid sequence of the human IF $DNA_{1-1254}$ (417 aa). SEQ ID NO: 24 represents the amino acid sequence of the mouse IF $DNA_{1-1254}$ (417 aa). SEQ ID NO: 25 represents the amino acid sequence of the rat IF $DNA_{1-1254}$ (421 aa). SEQ ID NO: 26 represents the amino acid sequence of the porcine IF DNA$_{14-1248}$ (411 aa). SEQ ID NO: 27 represents the amino acid sequence of the majority IF DNA$_{1-1254}$ (417 aa).

FIG. 7 illustrates the percent identity between the amino acid sequences of porcine intrinsic factor and human intrinsic factor, between the amino acid sequences of porcine intrinsic factor and rat intrinsic factor, and between the amino acid sequences of porcine intrinsic factor and mouse intrinsic factor.

DETAILED DESCRIPTION

Figure 1:
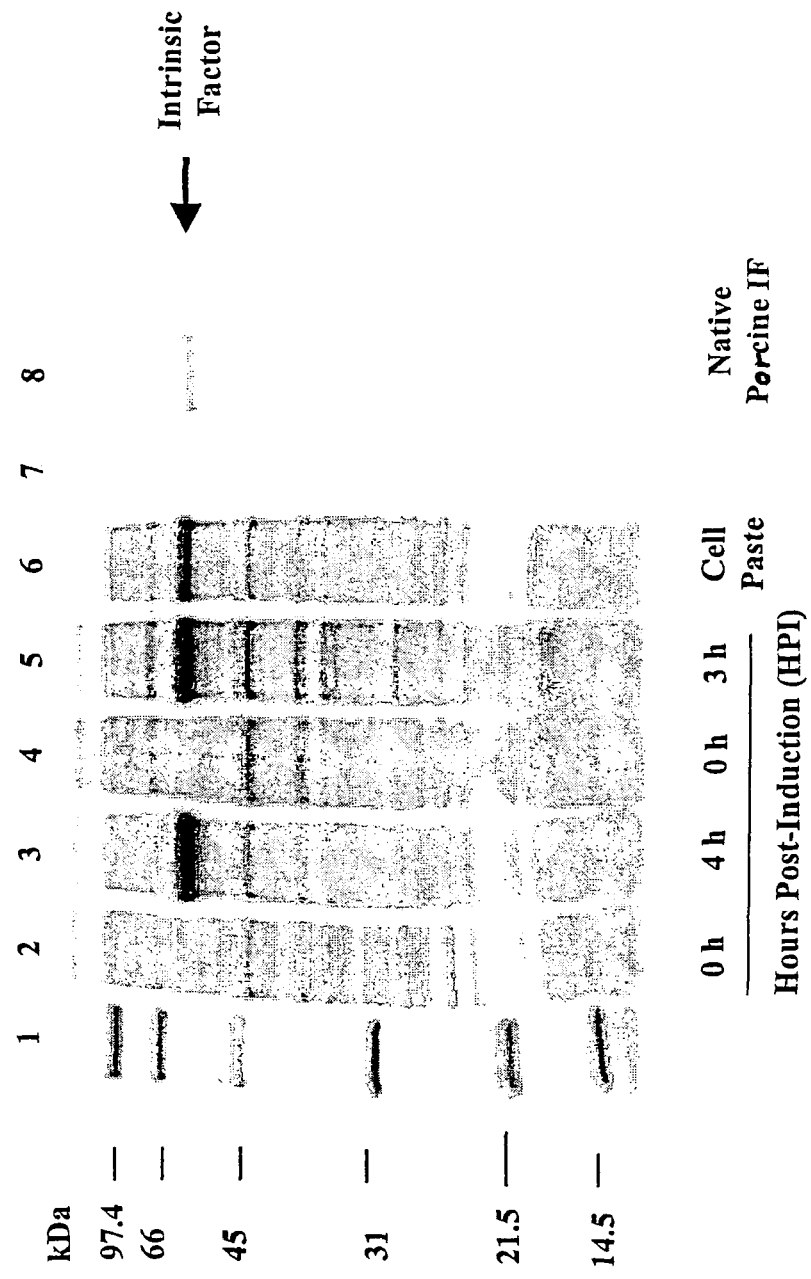
FIG. 1 illustrates the expression of recombinant porcine intrinsic factor. The *E. coli* cells were lysed and the proteins were resolved using SDS-PAGE (Sodium dodecyl sulfate polyacrylamide gel electrophoresis). Lane 1 contains molecular weight markers (marked in kilodaltons). Lanes 2 and 4 contain samples taken at 0 hour post-induction (0 HPI). Lanes 3 and 5 contain samples taken at 4 HPI and 3 HPI. Lane 6 represents the cellpaste (cells after concentration and centrifugation). Lane 8 contains the native porcine intrinsic factor (purified from hog (*Sus scrofa*) gut).

For purposes of the present invention, the term "fragment", with respect to a nucleotide sequence, is defined as a contiguous sequence of approximately at least 6, preferably at least about 8, more preferably at least about 10 nucleotides, and even more preferably at least about 15 nucleotides corresponding to a region of the specified nucleotide sequence.

The invention also includes a purified polypeptide which binds vitamin B$_{12}$ and has at least about 70% amino acid similarity or identity, preferably at least about 80% amino acid similarity or identity and more preferably at least about 85% amino acid similarity or identity to the amino acid sequences of SEQ ID NO: 3, SEQ ID NO: 6; or SEQ ID NO: 9 of the above-noted proteins which are, in turn, encoded by the above-described nucleotide sequences.

The term "identity" refers to the relatedness of two sequences on a nucleotide-by-nucleotide basis over a particular comparison window or segment. Thus, identity is defined as the degree of sameness, correspondence or equivalence between the same strands (either sense or antisense) of two DNA segments (or two amino acid sequences). "Percentage of sequence identity" is calculated by comparing two optimally aligned sequences over a particular region, determining the number of positions at which the identical base or amino acid occurs in both sequences in order to yield the number of matched positions, dividing the number of such positions by the total number of positions in the segment being compared and multiplying the result by 100. Optimal alignment of sequences may be conducted by the algorithm of Smith & Waterman, Appl. Math. 2:482 (1981), by the algorithm of Needleman & Wunsch, J. Mol. Biol. 48:443 (1970), by the method of Pearson & Lipman, Proc. Natl. Acad. Sci. (USA) 85:2444 (1988) and by computer programs which implement the relevant algorithms (e.g., Brutlag, Doug, Computational Molecular Biology Multiple Sequence Alignment [online], Feb. 7, 2007 [retrieved on Sep. 11, 2007]. Retrieved from the Internet:<URL: (http://cmgm.stanford.edu/biochem218/11Multiple.pdf≧; Higgins et al., CABIOS. 5L151-153 (1989)), FASTDB (Intelligenetics), BLAST (National Center for Biomedical Information; Altschul et al., Nucleic Acids Research 25:3389-3402 (1997)), PILEUP (Genetics Computer Group, Madison, Wis.) or GAP, BESTFIT, FASTA and TFASTA (Wisconsin Genetics Software Package Release 7.0, Genetics Computer Group, Madison, Wis.). (See U.S. Pat. No. 5,912,120.)

For purposes of the present invention, the term "complementarity" is defined as the degree of relatedness between two DNA segments. It is determined by measuring the ability of the sense strand of one DNA segment to hybridize with the anti-sense strand of the other DNA segment, under appropriate conditions, to form a double helix. The term "complement" is defined as a sequence which pairs to a given sequence based upon the canonic base-pairing rules. For example, a sequence A-G-T in one nucleotide strand is "complementary" to T-C-A in the other strand.

In the double helix, adenine appears in one strand, thymine appears in the other strand. Similarly, wherever guanine is found in one strand, cytosine is found in the other. The greater the relatedness between the nucleotide sequences of two DNA segments, the greater the ability to form hybrid duplexes between the strands of the two DNA segments.

The term "similarity", with respect to two amino acid sequences, is defined as the presence of a series of identical as well as conserved amino acid residues in both sequences. The higher the degree of similarity between two amino acid sequences, the higher the correspondence, sameness or equivalence of the two sequences. (The term "identity", with respect to two amino acid sequences, is defined as the presence of a series of exactly alike or invariant amino acid residues in both sequences.) The definitions of "complementarity", "identity" and "similarity" are well known to those of ordinary skill in the art.

The phrase "encoded by" refers to a nucleic acid sequence which codes for a polypeptide sequence, wherein the polypeptide sequence or a portion thereof contains an amino acid sequence of at least 3 amino acids, more preferably at least 8 amino acids, and even more preferably at least 15 amino acids from a polypeptide encoded by the nucleic acid sequence.

The present invention also encompasses an isolated nucleotide sequence which encodes porcine intrinsic factor and that is hybridizable, under moderately stringent conditions, to a nucleic acid having a nucleotide sequence comprising or complementary to the nucleotide sequences described above (see SEQ ID NO: 1, SEQ ID NO: 4, and SEQ ID NO: 7). A nucleic acid molecule is "hybridizable" to another nucleic acid molecule when a single-stranded form of the nucleic acid molecule can anneal to the other nucleic acid molecule under the appropriate conditions of temperature and ionic strength (see Sambrook et al., "Molecular Cloning: A Laboratory Manual, Second Edition (1989), Cold Spring Harbor Laboratory Press, Cold Spring Harbor, N.Y.)). The conditions of temperature and ionic strength determine the "stringency" of the hybridization.

The term "hybridization" as used herein is generally used to mean hybridization of nucleic acids at appropriate conditions of stringency as would be readily evident to those skilled in the art depending upon the nature of the probe sequence and target sequences. Conditions of hybridization and washing are well known in the art, and the adjustment of conditions depending upon the desired stringency by varying incubation time, temperature, and/or ionic strength of the solution are readily accomplished. See, for example, Sambrook, J. et al., Molecular Cloning: A Laboratory Manual, 2nd edition, Cold Spring Harbor Press, Cold Spring Harbor, N.Y., 1989, as noted above and incorporated herein by reference. (See also Short Protocols in Molecular Biology, ed. Ausubel et al. and Tijssen, Techniques in Biochemistry and Molecular Biology-Hybridization with Nucleic Acid Probes, "Overview of principles of hybridization and the strategy of nucleic acid assays" (1993), both incorporated herein by reference.) Specifically, the choice of conditions is dictated by the length of the sequences being hybridized, in particular, the length of the probe sequence, the relative G-C content of the nucleic acids and the amount of mismatches to be permitted. Low stringency conditions are preferred when partial hybridization between strands that have lesser degrees of complementarity is desired. When perfect or near perfect complementarity is desired, high stringency conditions are preferred. For typical high stringency conditions, the hybridization solution contains 6×S.S.C., 0.01 M EDTA, 1×Denhardt's solution and 0.5% SDS. Hybridization is carried out at about 68 degrees Celsius for about 3 to 4 hours for fragments of cloned DNA and for about 12 to about 16 hours for total eukaryotic DNA. For moderate stringencies, one may utilize filter pre-hybridizing and hybridizing with a solution of 3× sodium chloride, sodium citrate (SSC), 50% formamide (0.1 M of this buffer at pH 7.5) and 5×Denhardt's solution. One may then pre-hybridize at 37 degrees Celsius for 4 hours, followed by hybridization at 37 degrees Celsius with an amount of labeled probe equal to 3,000,000 cpm total for 16 hours, followed by a wash in 2×SSC and 0.1% SDS solution, a wash of 4 times for 1 minute each at room temperature and 4 times at 60 degrees Celsius for 30 minutes each. Subsequent to drying, one exposes to film. For lower stringencies, the temperature of hybridization is reduced to about 12 degrees Celsius below the melting temperature ($T_m$) of the duplex. The $T_m$ is known to be a function of the G-C content and duplex length as well as the ionic strength of the solution.

"Hybridization" requires that two nucleic acids contain complementary sequences. However, depending on the stringency of the hybridization, mismatches between bases may occur. As noted above, the appropriate stringency for hybridizing nucleic acids depends on the length of the nucleic acids and the degree of complementation. Such variables are well known in the art. More specifically, the greater the degree of similarity or homology between two nucleotide sequences, the greater the value of Tm for hybrids of nucleic acids having those sequences. For hybrids of greater than 100 nucleotides in length, equations for calculating Tm have been derived (see Sambrook et al., supra). For hybridization with shorter nucleic acids, the position of mismatches becomes more important, and the length of the oligonucleotide determines its specificity (see Sambrook et al., supra).

As used herein, the phrase "isolated nucleic acid fragment or sequence" means a polymer of RNA or DNA that is single-stranded or double-stranded, optionally containing synthetic, non-natural or altered nucleotide bases. An isolated nucleic acid fragment in the form of a polymer of DNA may be comprised of one or more segments of cDNA, genomic DNA or synthetic DNA. (The term "fragment", with respect to a specified polynucleotide, refers to a polynucleotide sequence which comprises a contiguous sequence of approximately at least about 6 nucleotides, preferably at least about 8 nucleotides, more preferably at least about 10 nucleotides, and even more preferably at least about 15 nucleotides, and most preferable at least about 25 nucleotides identical or complementary to a region of the specified nucleotide sequence.) Nucleotides (usually found in their 5'-monophosphate form) are referred to by their single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

The phrases "fragment or subfragment that is functionally equivalent" and "functionally equivalent fragment or subfragment" are used interchangeably herein. These phrases refer to a portion or subsequence of an isolated nucleic acid fragment in which the ability to alter gene expression or produce a certain phenotype is retained whether or not the fragment or subfragment encodes an active enzyme. For example, the fragment or subfragment can be used in the design of chimeric constructs to produce the desired phenotype in a transformed plant. Chimeric constructs can be designed for use in co-suppression or antisense by linking a nucleic acid fragment or subfragment thereof, whether or not it encodes an active enzyme, in the appropriate orientation relative to a plant promoter sequence.

The terms/phrases "homology", "homologous", "substantially similar" and "corresponding substantially" are used interchangeably herein. They refer to nucleic acid fragments wherein changes in one or more nucleotide bases does not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

The term "gene" refers to a nucleic acid fragment that expresses a specific protein, including regulatory sequences preceding (5' non-coding sequences) and following (3' non-coding sequences) the coding sequence.

The phrase "native gene" refers to a gene as found in nature with its own regulatory sequences. In contrast, the phrase "chimeric construct" refers to a combination of nucleic acid fragments that are not normally found together in nature. Accordingly, a chimeric construct may comprise regulatory sequences and coding sequences that are derived from different sources, or regulatory sequences and coding sequences derived from the same source, but arranged in a manner different than that normally found in nature. (The term "isolated" means that the sequence is removed from its natural environment.)

The phrase "foreign gene" refers to a gene not normally found in the host organism, but that is introduced into the host organism by gene transfer. Foreign genes can comprise native genes inserted into a non-native organism, or chimeric constructs. The term "transgene" means a gene that has been introduced into the genome by a transformation procedure.

The phrase "coding sequence" refers to a DNA sequence that codes for a specific amino acid sequence. The term "regulatory sequences" refers to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences.

The term "promoter" refers to a DNA sequence capable of controlling the expression of a coding sequence or functional RNA. The promoter sequence consists of proximal and more distal upstream elements, the latter elements often referred to as enhancers. Accordingly, the term "enhancer" means a DNA sequence that can stimulate promoter activity and may be an innate element of the promoter or a heterologous element inserted to enhance the level or tissue-specificity of a promoter. Promoter sequences can also be located within the transcribed portions of genes, and/or downstream of the transcribed sequences. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters that cause a gene to be expressed in most host cell types at most times are commonly referred to as "constitutive promoters". It is further recognized that since in most cases the exact boundaries of regulatory sequences have not been completely defined, DNA fragments of some variation may have identical promoter activity.

The term "intron" means an intervening sequence in a gene that does not encode a portion of the protein sequence. Thus, such sequences are transcribed into RNA but are then excised and are not translated. The term is also used for the excised RNA sequences. The term "exon" means a portion of the gene sequence that is transcribed and is found in the mature messenger RNA derived from the gene, but is not necessarily a part of the sequence that encodes the final gene product.

The phrase "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D. (1995) *Molecular Biotechnology* 3:225).

The phrase "3' non-coding sequences" refers to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., *Plant Cell* 1:671-680 (1989).

The phrase "RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. The phrase "messenger RNA (mRNA)" refers to the RNA that is without introns and that can be translated into protein by the cell. The term "cDNA" refers to a DNA that is complementary to and synthesized from a mRNA template using the enzyme reverse transcriptase. The cDNA can be single-stranded or converted into the double-stranded form using the Klenow fragment of DNA polymerase I. The phrase "sense RNA" refers to RNA transcript that includes the mRNA and can be translated into protein within a cell or in vitro.

The phrase "antisense RNA" refers to an RNA transcript that is complementary to all or part of a target primary transcript or mRNA and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. The phrase "functional RNA" refers to antisense RNA, ribozyme RNA, or other RNA that may not be translated but yet has an effect on cellular processes. The term "complement" and the phrase "reverse complement" are used interchangeably herein with respect to mRNA transcripts, and are meant to define the antisense RNA of the message.

The phrase "endogenous RNA" refers to any RNA which is encoded by any nucleic acid sequence present in the genome of the host prior to transformation with the recombinant construct of the present invention, whether naturally-occurring or non-naturally occurring, i.e., introduced by recombinant means, mutagenesis, etc.

The phrase "non-naturally occurring" means artificial, not consistent with what is normally found in nature.

The phrase "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation. In another example, the complementary RNA regions of the invention can be operably linked, either directly or indirectly, 5' to the target mRNA, or 3' to the target mRNA, or within the target mRNA, or a first complementary region is 5' and its complement is 3' to the target mRNA. "Operably linked" sequences include both expression control sequences that are contiguous with the gene of interest and expression control sequences that act in trans or at a distance to control the gene of interest. The phrase "expression control sequence" as used herein refers to polynucleotide sequences which are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The phrase "control sequences" is intended to include components whose presence is essential for expression and processing, and can also include additional components whose presence is advantageous, for example, leader sequences and fusion partner sequences.

The term "expression", as used herein, refers to the production of a functional end-product. Expression of a gene involves transcription of the gene and translation of the mRNA into a precursor or mature protein. "Antisense inhibition" refers to the production of antisense RNA transcripts capable of suppressing the expression of the target protein. The term "co-suppression" refers to the production of sense RNA transcripts capable of suppressing the expression of identical or substantially similar foreign or endogenous genes (U.S. Pat. No. 5,231,020).

The phrase "mature protein" refers to a post-translationally processed polypeptide; i.e., one from which any pre- or propeptides present in the primary translation product have been removed. The term "precursor" protein refers to the primary product of translation of mRNA; i.e., with pre- and pro-peptides still present. Pre- and pro-peptides may be but are not limited to intracellular localization signals.

The term "transformation", as defined herein, refers to any process by which exogenous DNA enters a host cell. Transformation may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells that transiently express the inserted DNA or RNA for limited periods of time.

The phrase "stable transformation" refers to the transfer of a nucleic acid fragment into a genome of a host organism, resulting in genetically stable inheritance. In contrast, the phrase "transient transformation" refers to the transfer of a nucleic acid fragment into the nucleus, or DNA-containing organelle, of a host organism resulting in gene expression without integration or stable inheritance. Host organisms containing the transformed nucleic acid fragments are referred to as "transgenic" organisms. The preferred method of cell transformation of rice, corn and other monocots is the use of particle-accelerated or "gene gun" transformation technology (Klein et al., (1987) *Nature* (London) 327:70-73; U.S. Pat. No. 4,945,050), or an *Agrobacterium*-mediated method using an appropriate Ti plasmid containing the transgene (Ishida Y. et al., 1996, *Nature Biotech.* 14:745-750). The term "transformation" as used herein refers to both stable transformation and transient transformation.

Standard recombinant DNA and molecular cloning techniques used herein are well known in the art and are described more fully in Sambrook, J., Fritsch, E. F. and Maniatis, T., *Molecular Cloning: A Laboratory Manual*; Cold Spring Harbor Laboratory Press: Cold Spring Harbor, 1989 (hereinafter "Sambrook").

The term "recombinant" refers to an artificial combination of two otherwise separated segments of sequence, e.g., by chemical synthesis or by the manipulation of isolated segments of nucleic acids by genetic engineering techniques.

The term "PCR" and the phrase "Polymerase Chain Reaction" refers to a technique for the synthesis of large quantities of specific DNA segments, consists of a series of repetitive cycles (Perkin Elmer Cetus Instruments, Norwalk, Conn.). Typically, the double stranded DNA is heat denatured, the two primers complementary to the 3' boundaries of the target segment are annealed at low temperature and then extended at an intermediate temperature. One set of these three consecutive steps is referred to as a cycle.

Polymerase chain reaction ("PCR") is a powerful technique used to amplify DNA millions of fold, by repeated replication of a template, in a short period of time. (Mullis et al., *Cold Spring Harbor Symp. Quant. Biol.* 51:263-273 (1986); Erlich et al., European Patent Application No. 50,424; European Patent Application No. 84,796; European Patent Application No. 258,017; European Patent Application No. 237,362; Mullis, European Patent Application No. 201,184; Mullis et al., U.S. Pat. No. 4,683,202; Erlich, U.S. Pat. No. 4,582,788; and Saiki et al., U.S. Pat. No. 4,683,194). The process utilizes sets of specific in vitro synthesized oligonucleotides to prime DNA synthesis. The design of the primers is dependent upon the sequences of DNA that are desired to be analyzed. The technique is carried out through many cycles (usually 20-50) of melting the template at high temperature, allowing the primers to anneal to complementary sequences within the template and then replicating the template with DNA polymerase.

The products of PCR reactions are analyzed by separation in agarose gels followed by ethidium bromide staining and visualization with UV transillumination. Alternatively, radioactive dNTPs can be added to the PCR in order to incorporate label into the products. In this case the products of PCR are visualized by exposure of the gel to x-ray film. The added advantage of radiolabeling PCR products is that the levels of individual amplification products can be quantitated.

The term "RT-PCR" means a combination of Reverse Transcription and PCR. Reverse transcription is a process where RNA is used as a starting material to make DNA using an enzyme called Reverse Transcriptase. The first strand of DNA that is made during reverse transcription is used as the starting material for the PCR reactions that follow.

The phrases "recombinant construct", "expression construct" and "recombinant expression construct" are used interchangeably herein. These phrases refer to a functional unit of genetic material that can be inserted into the genome of a cell using standard methodology well known to one skilled in the art. Such construct may be itself or may be used in conjunction with a vector. If a vector is used then the choice of vector is dependent upon the method that will be used to transform host plants as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the invention. The skilled artisan will also recognize that different independent transformation events will result in different levels and patterns of expression (Jones et al., (1985) *EMBO J.* 4:2411-2418; De Almeida et al., (1989) *Mol. Gen. Genetics* 218:78-86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

The term "polypeptide" as used herein, refers to any polymeric chain of amino acids. The terms "peptide" and "protein" are used interchangeably with the term polypeptide and also refer to a polymeric chain of amino acids. The term "polypeptide" encompasses native or artificial proteins, protein fragments and polypeptide analogs of a protein sequence. A polypeptide may be monomeric or polymeric.

The phrases "isolated protein" and "isolated polypeptide" refer to a protein or polypeptide that by virtue of its origin or source of derivation is not associated with naturally associated components that accompany it in its native state; is substantially free of other proteins from the same species; is expressed by a cell from a different species; or does not occur in nature. Thus, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art.

The phrases "specific binding" and "specifically binding", as used herein, in reference to the interaction of an antibody, a protein, or a peptide with a second chemical species, mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

The term "antibody", as used herein, broadly refers to any immunoglobulin (Ig) molecule comprised of four polypeptide chains, two heavy (H) chains and two light (L) chains, or any functional fragment, mutant, variant, or derivation thereof, which retains the essential epitope binding features of an Ig molecule. Such mutant, variant, or derivative antibody formats are known in the art, non-limiting embodiments of which are discussed below.

In a full-length antibody, each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4.

The phrase "antigen-binding portion" of an antibody (or simply "antibody portion"), as used herein, refers to one or more fragments of an antibody that retain the ability to specifically bind to an antigen (e.g., hIL-18). It has been shown that the antigen-binding function of an antibody can be performed by fragments of a full-length antibody. Such antibody embodiments may also be bispecific, dual specific, or multi-specific formats; specifically binding to two or more different antigens. Examples of binding fragments encompassed within the phrase "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which comprises a single variable domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the phrase "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123). Such antibody binding portions are known in the art (Kontermann and Dubel eds., *Antibody Engineering* (2001) Springer-Verlag. New York. 790 pp. (ISBN 3-540-41354-5).

Still further, an antibody or antigen-binding portion thereof may be part of a larger immunoadhesion molecules, formed by covalent or noncovalent association of the antibody or antibody portion with one or more other proteins or peptides. Examples of such immunoadhesion molecules include use of the streptavidin core region to make a tetrameric scFv molecule (Kipriyanov, S. M., et al. (1995) *Human Antibodies and Hybridomas* 6:93-101) and use of a cysteine residue, a marker peptide and a C-terminal polyhistidine tag to make bivalent and biotinylated scFv molecules (Kipriyanov, S. M., et al. (1994) *Mol. Immunol.* 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein.

The phrase "isolated antibody", as used herein, is intended to refer to an antibody that is substantially free of other antibodies having different antigenic specificities (e.g., an isolated antibody that specifically binds hIL-18 is substantially free of antibodies that specifically bind antigens other than hIL-18). An isolated antibody that specifically binds hIL-18 may, however, have cross-reactivity to other antigens, such as IL-18 molecules from other species. Moreover, an isolated antibody may be substantially free of other cellular material and/or chemicals.

A "monoclonal antibody" as used herein is intended to refer to a preparation of antibody molecules which share a common heavy chain and common light chain amino acid sequence, in contrast with "polyclonal" antibody preparations which contain a mixture of different antibodies. Monoclonal antibodies can be generated by several novel technologies like phage, bacteria, yeast or ribosomal display, as well as classical methods exemplified by hybridoma-derived antibodies (e.g., an antibody secreted by a hybridoma prepared by hybridoma technology, such as the standard Kohler and Milstein hybridoma methodology ((1975) Nature 256:495-497). Thus, a non-hybridoma-derived antibody of the invention is still referred to as a monoclonal antibody although it may have been derived by non-classical methodologies.

The phrase "recombinant antibody" refers to antibodies that are prepared, expressed, created or isolated by recombinant means, such as antibodies expressed using a recombinant expression vector transfected into a host cell, antibodies isolated from a recombinant, combinatorial antibody library, antibodies isolated from an animal (e.g., a mouse) that is transgenic for human immunoglobulin genes (see, e.g., Taylor et al. (1992) Nucleic Acids Research 20:6287-6295) or antibodies prepared, expressed, created or isolated by any other means that involves splicing of particular immunoglobulin gene sequences (such as human immunoglobulin gene sequences) to other DNA sequences. Examples of recombinant antibodies include chimeric, CDR-grafted and humanized antibodies.

The phrase "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the phrase "human antibody", as used herein, is not intended to include antibodies in which CDR sequences derived from the germline of another mammalian species, such as a mouse, have been grafted onto human framework sequences.

The phrase "recombinant human antibody", as used herein, is intended to include all human antibodies that are prepared, expressed, created or isolated by recombinant means, such as antibodies expressed using a recombinant expression vector transfected into a host cell, antibodies isolated from a recombinant, combinatorial human antibody library (Hoogenboom H. R., (1997) *TIB Tech.* 15:62-70; Azzazy H., and Highsmith W. E., (2002) *Clin. Biochem.* 35:425-445; Gavilondo J. V., and Larrick J. W. (2002) *BioTechniques* 29:128-145; Hoogenboom H., and Chames P. (2000) *Immunology Today* 21:371-378), antibodies isolated from an animal (e.g., a mouse) that is transgenic for human immunoglobulin genes (see e.g., Taylor, L. D., et al. (1992) Nucl. Acids Res. 20:6287-6295; Kellermann S-A., and Green L. L. (2002) *Current Opinion in Biotechnology* 13:593-597; Little M. et al (2000) *Immunology Today* 21:364-370) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The phrase "chimeric antibody" refers to antibodies which comprise heavy and light chain variable region sequences from one species and constant region sequences from another species, such as antibodies having murine heavy and light chain variable regions linked to human constant regions.

The phrase "CDR-grafted antibody" refers to antibodies which comprise heavy and light chain variable region sequences from one species but in which the sequences of one or more of the CDR regions of $V_H$ and/or VL are replaced with CDR sequences of another species, such as antibodies having murine heavy and light chain variable regions in which one or more of the murine CDRs (e.g., CDR3) has been replaced with human CDR sequences.

The phrase "humanized antibody" refers to antibodies which comprise heavy and light chain variable region sequences from a non-human species (e.g., a mouse) but in which at least a portion of the VH and/or VL sequence has been altered to be more "human-like", i.e., more similar to human germline variable sequences. One type of humanized antibody is a CDR-grafted antibody, in which human CDR sequences are introduced into non-human VH and VL sequences to replace the corresponding nonhuman CDR sequences.

The term "epitope" includes any polypeptide determinant capable of specific binding to an immunoglobulin or T-cell receptor. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics. An epitope is a region of an antigen that is bound by an antibody. In certain embodiments, an antibody is said to specifically bind an antigen when it preferentially recognizes its target antigen in a complex mixture of proteins and/or macromolecules.

The phrase "crystallized binding protein" as used herein, refers to a polypeptide that exists in the form of a crystal. Crystals are one form of the solid state of matter, which is distinct from other forms such as the amorphous solid state or the liquid crystalline state. Crystals are composed of regular, repeating, three-dimensional arrays of atoms, ions, molecules (e.g., proteins such as antibodies), or molecular assemblies (e.g., antigen/antibody complexes). These three-dimensional arrays are arranged according to specific mathematical relationships that are well-understood in the field. The fundamental unit, or building block, that is repeated in a crystal is called the asymmetric unit. Repetition of the asymmetric unit in an arrangement that conforms to a given, well-defined crystallographic symmetry provides the "unit cell" of the crystal. Repetition of the unit cell by regular translations in all three dimensions provides the crystal. See Giege, R. and Ducruix, A. Barrett, Crystallization of Nucleic Acids and Proteins, a Practical Approach, 2nd ea., pp. 20 1-16, Oxford University Press, New York, N.Y., (1999)."

The term "polynucleotide" as referred to herein means a polymeric form of two or more nucleotides, either ribonucleotides or deoxynucleotides or a modified form of either type of nucleotide. The term includes single and double stranded forms of DNA but preferably is double-stranded DNA.

The phrase "isolated polynucleotide" as used herein means a polynucleotide (e.g., of genomic, cDNA, or synthetic origin, or some combination thereof) that, by virtue of its origin, the "isolated polynucleotide" is not associated with all or a portion of a polynucleotide with which the "isolated polynucleotide" is found in nature; is operably linked to a polynucleotide that it is not linked to in nature; or does not occur in nature as part of a larger sequence.

The term "vector", as used herein, is intended to refer to a nucleic acid molecule capable of transporting another nucleic acid to which it has been linked. One type of vector is a "plasmid", which term refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, the terms "plasmid" and "vector" may be used interchangeably, as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The phrase "recombinant host cell" (or simply "host cell"), as used herein, is intended to refer to a cell into which exogenous DNA has been introduced. It should be understood that such phrases are intended to refer not only to the particular subject cell, but, to the progeny of such a cell. Because certain modifications may occur in succeeding generations due to either mutation or environmental influences, such progeny may not, in fact, be identical to the parent cell, but are still included within the scope of the phrase "host cell" as used herein. Preferably host cells include prokaryotic and eukaryotic cells selected from any of the Kingdoms of life. Preferred eukaryotic cells include protist, fungal, plant and animal cells. Most preferably host cells include but are not limited to the prokaryotic cell line *E. Coli*; mammalian cell lines CHO and COS; the insect cell line Sf9; and the fungal cell *Saccharomyces cerevisiae*.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)), which is incorporated herein by reference for any purpose.

The term "primer" means an oligonucleotide or a short single-stranded nucleic acid molecule that binds to the DNA sequence of interest and acts as a starting point for the synthesis of nucleic acids from the DNA sequence of interest.

The term "sample", as used herein, is used in its broadest sense. A "biological sample", as used herein, includes, but is not limited to, any quantity of a substance from a living thing or formerly living thing. Such living things include, but are not limited to, humans, mice, rats, monkeys, dogs, rabbits and other animals. Such substances include, but are not limited to, blood, serum, urine, synovial fluid, cells, organs, tissues, bone marrow, lymph nodes and spleen.

This invention relates to the porcine intrinsic factor protein, to the nucleic acid molecules encoding porcine intrinsic factor, to antibodies raised against porcine intrinsic factor, and to inhibitory compounds that regulate porcine intrinsic factor. This invention also provides methods for identifying and obtaining the protein porcine intrinsic factor, the nucleic acid molecule of porcine intrinsic factor, and antibodies to the porcine intrinsic factor and portions of those antibodies. This invention also demonstrates the use of this protein in diagnostic assays.

The method for producing the porcine intrinsic factor of this invention involves the following steps:
(a) isolating total RNA from porcine stomach tissue;
(b) cloning cDNA encoding porcine intrinsic factor by RT-PCR;
(c) inserting porcine intrinsic factor cDNA into an expression vector;
(d) expressing the recombinant intrinsic factor protein in a host cell system for a period of time and under conditions suitable for expression of the protein; and
(e) purifying the intrinsic factor protein.

The invention also involves checking for the binding activity of intrinsic factor to vitamin $B_{12}$. The invention further involves testing the feasibility of using recombinant intrinsic factor in automated immunoassay analyzer.

The recombinant porcine intrinsic factor of this invention can be used in diagnostic assays to detect the levels of vitamin $B_{12}$ in biological samples.

The Vitamin $B_{12}$ Diagnostic Assay is part of the menu in platforms for diagnostic analyzers having such trademarks "IMx", "AxSYM" and "ARCHITECT", all of which are commercially available from Abbott Laboratories, Abbott Park, Ill. The intended use of the assay is for the quantitative determination of the vitamin $B_{12}$ in human serum and plasma. The vitamin $B_{12}$ assay for the "IMx" and "AxSYM" analyzers is based on the Microparticle Enzyme Immunoassay (MEIA) technology. The vitamin $B_{12}$ assay for the "ARCHITECT" analyzer is a Chemiluminescent Microparticle Immunoassay (CMIA).

Intrinsic factor is produced in the stomach. It binds to vitamin $B_{12}$ in the proximal small intestine, thereby forming a complex with vitamin $B_{12}$. This intact complex moves through the intestine until reaches the distal ileum, where it binds to high-affinity receptors, specific for intrinsic factor, located on the luminal surface of ileal absorptive cells (enterocytes). The intrinsic factor—vitamin $B_{12}$ complex attaches to these surface receptors rapidly, enters these cells, and finally reaches the portal circulation. Thus, the intrinsic factor helps in the transport and absorption of vitamin $B_{12}$ in the intestine. The ability of the intrinsic factor to specifically bind vitamin $B_{12}$ is used as the premise in the diagnostic assays developed at Abbott Laboratories, Abbott Park, Ill. The level of vitamin $B_{12}$ in a biological sample is determinative of how much vitamin $B_{12}$ is bound to particles coated with intrinsic factor.

Figure 4:
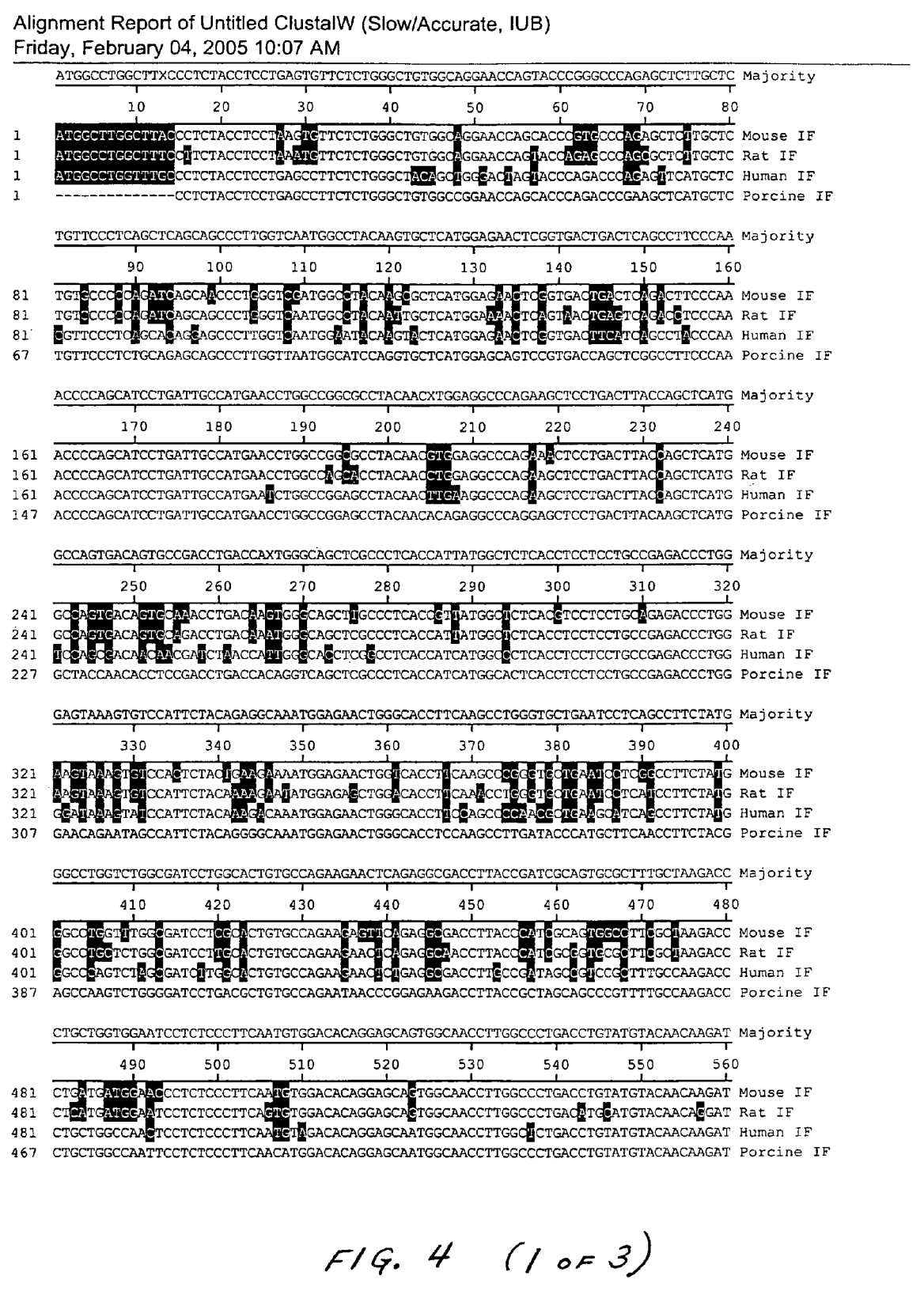

The percent identity between the nucleotide sequence of porcine intrinsic factor and human intrinsic factor is 83% (see FIGS. 4 and 5). The percent identity between the nucleotide sequence of porcine intrinsic factor and mouse intrinsic factor is 79% (see FIGS. 4 and 5). The percent identity between the nucleotide sequence of porcine intrinsic factor and rat intrinsic factor is 79% (see FIGS. 4 and 5). The percent identity between the amino acid sequence of porcine intrinsic factor and human intrinsic factor is 81% (see FIGS. 6 and 7). The percent identity between the amino acid sequence of porcine intrinsic factor and mouse intrinsic factor is 73% (see FIGS. 6 and 7). The percent identity between the amino acid sequence of porcine intrinsic factor and rat intrinsic factor is 72% (see FIGS. 6 and 7).

Production of the Recombinant Porcine Intrinsic Factor

Once the gene encoding the porcine intrinsic factor has been isolated, it may then be introduced into either a prokaryotic or eukaryotic host cell through the use of a vector or construct. The vector, for example, a bacteriophage, cosmid or plasmid, may comprise the nucleotide sequence encoding the porcine intrinsic factor, as well as any regulatory sequence (e.g., promoter) which is functional in the host cell and is able to elicit expression of the porcine intrinsic factor encoded by the nucleotide sequence. The regulatory sequence (e.g., promoter) is in operable association with, or operably linked to, the nucleotide sequence. (A promoter is said to be "operably linked" with a coding sequence if the promoter affects transcription or expression of the coding sequence.) Suitable promoters include, for example, those from genes encoding alcohol dehydrogenase, glyceraldehyde-3-phosphate dehydrogenase, phosphoglucoisomerase, phosphoglycerate kinase, acid phosphatase, T7, TPI, lactase, metallothionein, cytomegalovirus immediate early, whey acidic protein, glucoamylase, and promoters activated in the presence of galactose, for example, GA1 and GAL10. Additionally, nucleotide sequences which encode other proteins, oligosaccharides, lipids, etc. may also be included within the vector as well as other regulatory sequences such as a polyadenylation signal (e.g., the poly-A signal of SV-40T-antigen, ovalalbumin or bovine growth hormone). The choice of sequences present in the construct is dependent upon the desired expression products as well as the nature of the host cell.

As noted above, once the vector has been constructed, it may then be introduced into the host cell of choice by methods known to those of ordinary skill in the art including, for example, transfection, transformation and electroporation (see *Molecular Cloning: A Laboratory Manual*, $2^{nd}$ ed., Vol. 1-3, ed. Sambrook et al., Cold Spring Harbor Laboratory Press (1989)). The host cell is then cultured under suitable conditions permitting expression of the genes leading to the production of the desired porcine intrinsic factor, which is then recovered and purified.

Examples of suitable prokaryotic host cells include, for example, bacteria such as *Escherichia coli, Bacillus subtilis* as well as Cyanobacteria such as *Spirulina* spp. (i.e., blue-green algae). Examples of suitable eukaryotic host cells include, for example, mammalian cells, plant cells, yeast cells such as *Saccharomyces cerevisiae, Saccharomyces carlsbergensis, Lipomyces starkey, Candida* spp. such as *Yarrowia*

(*Candida*) *lipolytica*, *Kluyveromyces* spp., *Pichia* spp., *Trichoderma* spp. or *Hansenula* spp., or fungal cells such as filamentous fungal cells, for example, *Aspergillus*, *Neurospora* and *Penicillium*. Preferably, *Saccharomyces cerevisiae* (baker's yeast) cells are utilized.

Expression in a host cell can be accomplished in a transient or stable fashion. Transient expression can occur from introduced constructs which contain expression signals functional in the host cell, but which constructs do not replicate and rarely integrate in the host cell, or when the host cell is not proliferating. Transient expression also can be accomplished by inducing the activity of a regulatable promoter operably linked to the gene of interest, although such inducible systems frequently exhibit a low basal level of expression. Stable expression can be achieved by introduction of a construct that can integrate into the host genome or that autonomously replicates in the host cell. Stable expression of the gene of interest can be selected through the use of a selectable marker located on or transfected with the expression construct, followed by selection for cells expressing the marker. When stable expression results from integration, the site of the construct's integration can occur randomly within the host genome or can be targeted through the use of constructs containing regions of homology with the host genome sufficient to target recombination with the host locus. Where constructs are targeted to an endogenous locus, all or some of the transcriptional and translational regulatory regions can be provided by the endogenous locus.

To prepare an antibody of the invention, the antibody is raised against an antigen (i.e., the porcine intrinsic factor or fragment thereof) capable of eliciting production of the antibody. The present invention includes the isolated antibody or antibodies raised against the antigen, as well as antibody portions or fragments thereof. Further, the antibodies of the invention include monoclonal and recombinant antibodies, and portions or fragments thereof. In various embodiments, the antibody, or portion thereof, may comprise amino acid sequences derived entirely from a single species, such as a fully human or fully mouse antibody, or portion thereof. In other embodiments, the antibody, or portion thereof, may be a chimeric antibody or a CDR-grafted antibody (CDR, complementary determining region) or other form of humanized antibody.

Isolation of the nucleic acid molecule of the present invention was unexpected because initial attempts to obtain nucleic acid molecules using RT-PCR were unsuccessful. After numerous attempts (i.e., a total of 10 attempts), specific primers that were useful for isolating such nucleic acid molecules were discovered. The cDNA sequence of the porcine intrinsic factor that can be used to produce recombinant intrinsic factor protein is now known. This recombinant protein can be used in diagnostic assays to detect levels of vitamin $B_{12}$ in biological samples (blood, plasma) of patients.

The following non-limiting examples further illustrate this invention.

Example I

Cloning of Porcine Intrinsic Factor

Porcine intrinsic factor was produced by the parietal cells of the porcine stomach. Because the parietal cells are highly concentrated in the fundic region of the stomach, the fundic region was used for total RNA isolation. The stomach tissue stored in "RNA Later" solution (purchased from Ambion, Inc., Austin, Tex.) was homogenized in "TRIzol" reagent (purchased from Invitrogen, Carlsbad, Calif.), and total RNA was isolated using the protocol recommended by the vendor. The total RNA isolated from the porcine stomach was used as the starting material in the Reverse Transcriptase Polymerase Chain Reaction (RT-PCR) reactions. The designs of the primers for RT-PCR were based on the known homology between human, mouse, and rat intrinsic factor. The first six RT-PCR runs, each of which involved different reaction conditions, failed to produce the porcine intrinsic factor cDNA. Additional primers (i.e., a total of 8 primers) were made and were used in all possible combinations in the seventh RT-PCR run. In this seventh RT-PCR run, a porcine intrinsic factor cDNA fragment, referred to herein as Porcine IF $cDNA_{200-1254}$ (1054 bp in length, SEQ ID NO: 1, its reverse complement SEQ ID NO: 2, and its amino acid sequence SEQ ID NO: 3), was obtained using the Forward Primer huIF200For (SEQ ID NO: 10) and Reverse Primer huIF Reverse 1 (SEQ ID NO: 11). The RT-PCR profile was as follows: RT step was performed at a temperature of 42° C. for 25 minutes. This step was followed by the PCR step, which included one initial denaturation step at a temperature of 94° C. for 30 seconds; then 40 cycles of the following conditions: a temperature of 94° C. for 30 seconds, then a temperature of 57° C. for 30 seconds, then a temperature of 72° C. for 1 minute; followed by a final extension at a temperature of 72° C. for 5 minutes. To obtain full-length porcine intrinsic factor cDNA, additional primers (i.e., a total of 9 primers) were made, and RT-PCR runs were performed. The first four RT-PCR runs, each of which involved different reaction conditions, failed to produce the porcine intrinsic factor cDNA. In the fifth RT-PCR run, a porcine intrinsic factor cDNA fragment (1234 bp in length), referred to herein as Porcine IF $cDNA_{14-1248}$, was obtained using Forward Primer huIF-For14 (SEQ ID NO: 12) and Reverse Primer huIF 1248Rev (SEQ ID NO: 13). The RT-PCR profile was as follows: RT step was performed at a temperature of 42° C. for 40 minutes. This step was followed by the PCR step which included one initial denaturation step at a temperature of 99° C. for 4 minutes; then 43 cycles of the following conditions: temperature of 95° C. for 30 seconds, then a temperature of 61° C. for 30 seconds, then a temperature of 72° C. for 1 minute; followed by a final extension at a temperature of 72° C. for 0.5 minute. This cDNA fragment (1234 bp in length), referred to herein as Porcine IF $cDNA_{14-1248}$, (denoted by SEQ ID NO: 4, and its reverse complement SEQ ID NO: 5 and its amino acid sequence SEQ ID NO: 6) was cloned into the TA cloning vector (pCR 2.1, purchased from Invitrogen, Carlsbad, Calif.) and transformed into "Top10" *E. coli* cells (Invitrogen, Carlsbad, Calif.) to produce the Porcine IF $cDNA_{14-1248}$ (SEQ ID NO: 5).

The Porcine IF $cDNA_{14-1248}$ (SEQ ID NO: 5) was used as the template to produce the cDNA sequence encoding the porcine intrinsic factor mature peptide, referred to herein as Porcine IF $cDNA_{54-1254}$-Mature Peptide. The nucleotide sequence of the coding strand of Porcine IF $cDNA_{54-1254}$-Mature Peptide (1200 bp in length) is denoted by SEQ ID NO: 7, its reverse complement is denoted by SEQ ID NO: 8. Translation of the open reading frame in SEQ ID NO: 7 suggests that porcine intrinsic factor mature peptide contains 399 amino acids, with an amino acid sequence denoted by SEQ ID NO: 9. The encoded mature peptide has a predicted molecular weight of ~44 kDa.

Using the Porcine IF $cDNA_{14-1248}$ (SEQ ID NO: 5) as the template and the Forward Primer pIFMP-ForI (SEQ ID NO: 14) and Reverse Primer pIFMP-RevXhoI (SEQ ID NO: 15), the cDNA encoding the Porcine IF $cDNA_{54-1254}$-Mature Peptide was amplified by PCR. The PCR profile was as follows: one initial denaturation step at a temperature of 95° C. for 5 minutes; then 33 cycles of the following conditions: a temperature of 95° C. for 30 seconds, then a temperature of 57° C. for 30 seconds, then a temperature of 72° C. for 1 minute; followed by a final extension at a temperature of 72° C. for 5 minutes. This PCR fragment was subcloned into pGEMEX-1 expression vector (purchased from Promega Corporation, Madison, Wis.). The expressed protein was insoluble and formed inclusion bodies.

To produce a soluble version of this protein, cDNA encoding the Porcine IF $cDNA_{54-1254}$-Mature Peptide was amplified by PCR using IF $cDNA_{14-1248}$ (SEQ ID NO: 5) as the template and the Forward primer pIF-PIC-MP-For EcoR1 (SEQ ID NO: 16) and the Reverse pIF-MP-pMAL-SalI Rev primer (SEQ ID NO: 17) and the following PCR conditions: one initial denaturation step at a temperature of 95° C. for 5 minutes; then 35 cycles of the following conditions: a temperature of 95° C. for 30 seconds, then a temperature of 56° C. for 30 seconds, then a temperature of 72° C. for 1 minute; followed by a final extension at a temperature of 72° C. for 5 minutes. The resultant PCR was introduced into the pMAL expression vector (purchased from Invitrogen, Carlsbad, Calif.) to create the plasmid pMAL-IF. This plasmid (pMAL-IF) produces porcine intrinsic factor as a fusion protein with Maltose Binding Protein (MBP; molecular weight ~43 kDa). The predicted molecular weight of the pMAL-IF fusion protein is ~87 kDa. The MBP component rendered the porcine intrinsic factor protein partially soluble.

To further increase the solubility of the protein and to enhance proper protein folding, the cDNA insert encoding the Porcine IF $cDNA_{54-1254}$-Mature Peptide was excised from pMAL-IF using the restriction enzymes EcoRI and SalI and inserted into pET32a vector (purchased from Novagen, Madison, Wis.) digested with EcoRI and SalI. This vector produces porcine intrinsic factor as a fusion protein with Thioredoxin protein (TrX; molecular weight ~18 kDa). The predicted molecular weight of the pET32a-IF fusion protein is ~62 kDa. The TrX component rendered the porcine intrinsic factor protein partially soluble.

Example II

Expression of Recombinant Porcine Intrinsic Factor in *E. coli*

Recombinant porcine intrinsic factor was produced in *E. coli* by expressing the protein from the pMAL-IF vector as well as the pET32a-IF vector by induction of the T7 promoter using IPTG (isopropyl-beta-D-thiogalactopyranoside). The cells were harvested for three hours after induction in one case and for four hours after induction in another case. The harvested *E. coli* cells were lysed and the cell lysate was clarified by centrifugation. The clarified lysate was loaded onto an anti-intrinsic factor antibody affinity column. The recombinant intrinsic factor bound to the affinity column. The column was washed with phosphate buffered saline (PBS) buffer to remove any unbound proteins. The intrinsic factor that bound to the column was eluted with glycine buffer. Referring now to FIG. 1, Lane 1 contains molecular weight markers (marked in kilodaltons). Lanes 2 and 4 contain samples taken at 0 hour post-induction (0 HPI). Lanes 3 and 5 contain samples taken at 4 HPI and 3 HPI. Lane 6 represents the cellpaste (cells after concentration and centrifugation). Lane 8 contains the native porcine intrinsic factor (purified from hog (*Sus scrofa*) gut).

Example III

Demonstration of the Binding Activity of Porcine Intrinsic Factor

A. Binding to Vitamin $B_{12}$ in Conjugate Blots

Figure 2:
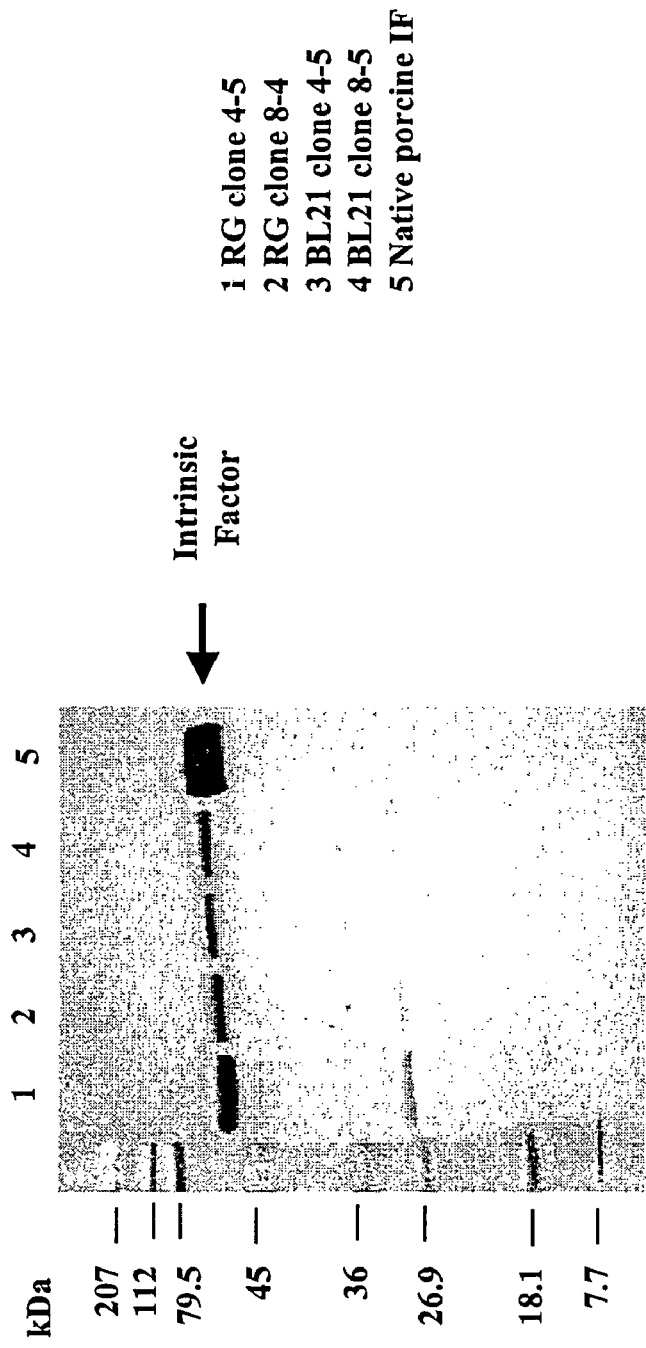
FIG. 2 illustrates the binding of recombinant porcine intrinsic factor to vitamin $B_{12}$. The *E. coli* cells were lysed and the proteins were resolved using SDS-PAGE and blotted onto a nitrocellulose membrane. The membrane was probed with vitamin $B_{12}$ conjugate to alkaline phosphatase. Protein bands that bound vitamin $B_{12}$ were identified by incubation with alkaline phosphatase substrates that develop color. Lane 1 contains molecular weight markers (marked in kilodaltons). Lanes 2, 3, 4, and 5 represent cells from various clones expressing recombinant porcine intrinsic factor. Lane 6 contains the native porcine intrinsic factor (purified from hog (*Sus scrofa*) gut). The recombinant intrinsic factor protein band developed color, thereby demonstrating that the intrinsic factor bound vitamin $B_{12}$.

The recombinant porcine intrinsic factor bound to vitamin $B_{12}$ as demonstrated using a vitamin $B_{12}$-Alkaline Phosphatase conjugate blot. The *E. coli* lysate containing the expressed recombinant porcine intrinsic factor was run on an SDS-PAGE (Polyacrylamide Gel Electrophoresis), and the gel was blotted onto nitrocellulose. This blot was probed with vitamin $B_{12}$-alkaline phosphatase conjugate and developed using an appropriate substrate. The recombinant intrinsic factor protein band developed color, thereby demonstrating that the intrinsic factor bound vitamin $B_{12}$. Referring now to FIG. 2, Lane 1 contains molecular weight markers (marked in kilodaltons). Lanes 2, 3, 4, and 5 represent cells from various clones expressing recombinant porcine intrinsic factor. Lane 6 contains the native porcine intrinsic factor (purified from hog (*Sus scrofa*) gut). The recombinant intrinsic factor protein band developed color, thereby demonstrating that the intrinsic factor bound vitamin $B_{12}$.

B. Binding to Anti-Intrinsic Factor Antibody in Western Blots

Binding of the recombinant porcine intrinsic factor to anti-intrinsic factor antibody was demonstrated by using Western blotting. The *E. Coli* lysate containing the expressed recombinant porcine intrinsic factor was run on an SDS-PAGE (Polyacrylamide Gel Electrophoresis), and the gel was blotted onto nitrocellulose. This blot was probed with anti-intrinsic factor antibody and developed using an appropriate substrate. The recombinant intrinsic factor protein band developed color, thereby demonstrating that the recombinant intrinsic factor was recognized by the antibody. Referring now to FIG. 3, Lane 1 contains molecular weight markers (marked in kilodaltons). Lanes 2, 3, 4, and 5 represent cells from various clones expressing recombinant porcine intrinsic factor. Lane 6 contains the native porcine intrinsic factor (purified from hog (*Sus scrofa*) gut). The recombinant intrinsic factor protein band developed color, thereby demonstrating that the recombinant intrinsic factor was recognized by the antibody.

C. Feasibility of Using Recombinant Porcine Intrinsic Factor in "AxSYM" and "ARCHITECT" Diagnostic Assays for Vitamin $B_{12}$ The vitamin $B_{12}$-binding capacity of the recombinant porcine Intrinsic Factor was measured using in "ARCHITECT" Intrinsic Factor Binding Capacity Assay. The assay is a one-step competitive assay where intrinsic factor from the test sample competes with intrinsic factor coated onto microparticles for the vitamin $B_{12}$-acridinium tracer. Thus, signal in the assay is inversely proportional to the concentration of intrinsic factor in the test sample. The results are read from a vitamin $B_{12}$ calibration curve, and the vitamin $B_{12}$ concentration results are converted to binding capacity using an equation. The Binding Capacity Value for the recombinant porcine intrinsic factor was determined to be 904 ng/ml.

Example IV

The "ARCHITECT" B12 assay is a two-step assay with an automated sample pretreatment, for determining the presence of vitamin $B_{12}$ in human serum and plasma using Chemiluminescent Microparticle Immunoassay (CMIA) technology with flexible assay protocols. The "ARCHITECT" analyzer and the method for using the "ARCHITECT" analyzer are described in U.S. Pat. No. 5,795,784, the entirety of which is incorporated herein by reference. The assay for vitamin $B_{12}$ is described in ARCHITECT™ System B12, List No. 6C09, 69-0689/R1, December 1998, Abbott Laboratories, Abbott Park, Ill., the entirety of which is incorporated herein by reference. The sample and Pre-Treatment Reagent 1, Pre-Treatment Reagent 2, and Pre-Treatment Reagent 3 are combined. An aliquot of the pre-treated sample is aspirated and transferred into a new reaction vessel. The pre-treated sample, assay diluent, and intrinsic factor coated paramagnetic microparticles are combined. Vitamin $B_{12}$ present in the sample binds to the intrinsic factor coated microparticles. After washing, vitamin $B_{12}$-acridinium-labeled conjugate is added in the second step. The vitamin $B_{12}$-acridinium-labeled conjugate is capable of undergoing a chemiluminescent reaction. Pre-Trigger and Trigger solutions are then added to the reaction mixture; the resulting chemiluminescent reaction is measured as relative light units. An inverse relationship exists between the amount of vitamin $B_{12}$ in the sample and the relative light units detected by the "ARCHITECT" i optical system. Further details on the system and assay technology can be found in "ARCHITECT" i System Operations Manual, the entirety of which is incorporated herein by reference. The reagents for the assay are described below (the amounts per bottle are for 100 tests):

Porcine intrinsic factor coated Microparticles in borate buffer with protein (bovine) stabilizers. Preservative: antimicrobial agents. (1 bottle, 6.6 mL/bottle)

B12 acridinium-labeled Conjugate in MES buffer. Minimum concentration: 0.7 ng/mL. Preservative: antimicrobial agent. (1 bottle, 5.9 mL/bottle)

B12 Assay Diluent containing borate buffer with EDTA. Preservative: antimicrobial agents. (1 bottle, 10 ml/bottle)

B12 Pre-Treatment Reagent 1 containing 1.0 N sodium hydroxide with 0.005% potassium cyanide. (1 bottle, 27 mL/bottle)

B12 Pre-Treatment Reagent 2 containing alpha monothioglycerol and EDTA. (1 bottle, 5.5 mL/bottle)

B12 Pre-Treatment Reagent 3 containing cobinamide dicyanide in borate buffer with protein (avian) stabilizers. Preservative: Sodium Azide. (1 bottle, 5.5 mL/bottle)

"ARCHITECT" i Multi-Assay Manual Diluent containing phosphate buffered saline solution. Preservative: antimicrobial agent. (1 bottle, 100 mL/bottle)

"ARCHITECT" i Pre-Trigger Solution containing 1.32% (w/v) hydrogen peroxide.

"ARCHITECT" i Trigger Solution containing 0.35 N sodium hydroxide.

"ARCHITECT" i Wash Buffer containing phosphate buffered saline solution. Preservative: antimicrobial agent.

Example V

The "AxSYM" B12 assay is based on the Microparticle Enzyme Immunoassay (MEIA) technology. The "AxSYM" analyzer and the method for using the "AxSYM" analyzer are described in U.S. Pat. No. 5,358,691, the entirety of which is incorporated herein by reference. The assay for vitamin $B_{12}$ is discussed in Abbott AxSYM® System B12, List No. 3C79, 69-0912/R2, February 1999, Abbott Laboratories, Abbott Park, Ill., the entirety of which is incorporated herein by reference.

The "AxSYM" B12 reagents and sample are pipetted in the following sequence:

The sample and all "AxSYM" B12 reagents required for one test are pipetted by the Sampling Probe into various wells of a Reaction Vessel. Extractant 1 and Extractant 2 are combined in one Reaction Vessel well. Sample, Denaturant, and a portion of the Extractant mixture are combined in another Reaction vessel well. The Reaction Vessel is immediately transferred into the Processing Center. Further pipetting is carried out in the Processing center with the Processing Probe. Intrinsic factor coated microparticles are added to the reaction mixture. Vitamin $B_{12}$ present in the sample binds to the intrinsic factor coated microparticles forming a complex containing vitamin $B_{12}$ and intrinsic factor coated microparticles. An aliquot of the reaction mixture is transferred to the matrix cell. The microparticles bind irreversibly to the glass fiber matrix. The matrix cell is washed to remove materials not bound to the microparticles. The vitamin $B_{12}$:Alkaline Phosphatase Conjugate is dispensed onto the matrix cell, thereby forming a complex containing vitamin $B_{12}$, intrinsic factor coated microparticles, and conjugate. The vitamin $B_{12}$:Alkaline Phosphatase Conjugate is capable of forming a fluorescent product. The matrix cell is washed to remove unbound conjugate. The substrate, 4-Methylumbelliferyl Phosphate, is added to the matrix cell and the fluorescent product is measured by the MEIA optical assembly. The substrate, 4-Methylumbelliferyl Phosphate, is a fluorogenic material. Further details on the system and assay technology can be found in "AxSYM" System Operations Manual, the entirety of which is incorporated herein by reference. The reagents for the assay are described below (the amounts per bottle, for the items in the REAGENT PACK, are for 100 tests):

Reagent Pack

B12 Denaturant

B12 Denaturant: 0.8 N Sodium Hydroxide with 0.005% Potassium Cyanide supplied in a separate bottle from the Dual Pack (1 bottle, 13.0 mL/per bottle)

Reagent Pack A

Extractant 1. Cobinamide Dicyanide in borate buffer with protein (avian) stabilizer. Preservative: Sodium Azide. (1 bottle, 8.7 mL/bottle)

Extractant 2. Alpha Monothioglycerol in EDTA. (1 bottle, 3.8 mL/bottle)

Porcine Intrinsic Factor Coated Microparticles in borate buffer with protein (bovine) stabilizer. Preservative: Sodium Azide. (1 bottle, 14.1 mL/bottle)

Reagent Pack B

B12:Alkaline Phosphatase (bovine) Conjugate in TRIS buffer with protein (bovine) stabilizer. Minimum concentration: 0.1 µg/mL. Preservative: Sodium Azide. (1 bottle, 12.5 mL/bottle)

B12 Denaturant. 0.8 N Sodium Hydroxide with 0.005% Potassium Cyanide. (1 bottle, 13.0 mL/bottle)

Porcine Intrinsic Factor Coated Microparticles in borate buffer with protein (bovine) stabilizer. Preservative: Sodium Azide. (1 bottle, 14.1 mL/bottle)

Other Reagents (not in Reagent Pack)

Solution 1 (MUP) contains 4-Methylumbelliferyl Phosphate, 1.2 mM, in AMP buffer. Preservative: Sodium Azide. (4 bottles, 230 mL/bottle)

Solution 3 (Matrix Cell Wash) contains 0.3 M sodium chloride in TRIS buffer. Preservatives: Sodium Azide and Antimicrobial Agents (4 bottles, 100 mL/bottle)

Solution 4 (Line diluent) contains 0.1 M phosphate buffer. Preservatives: Sodium Azide and Antimicrobial Agent (1 bottle, 10 L/bottle)

AxSYM Probe Cleaning Solution contains 2% Tetraethylammonium Hydroxide (TEAH) (2 bottles, 220 mL/bottle)

Porcine intrinsic factor coated microparticles are typically made of material such as polystyrene and they range from about 0.5 micrometer to about 15 micrometer in diameter. The microparticles have functional groups on the surface thereof, such as, for example, carboxyl groups or amino groups, which are used for coupling to proteins or other molecules. This coupling can be passive or active. In active coupling, an activating reagent, such as, for example, EDAC, is used.

For porcine intrinsic factor coated microparticles for use in the "ARCHITECT" B12 assay, the porcine intrinsic factor is covalently coupled to Carboxylated Microparticles by using EDAC activation method. EDAC (1-ethyl-3-(-dimethylaminopropyl)-carbodiimide hydrochloride) is used to activate carboxyl groups on the microparticle, which groups can undergo coupling with amino groups on the protein (i.e., the porcine intrinsic factor).

For porcine intrinsic factor coated microparticles for us in the "AxSYM" B12 assay, the anti-intrinsic factor antibody is first coupled to the microparticles using EDAC. Then the porcine intrinsic factor is added to these microparticles. The porcine intrinsic factor binds to the anti-intrinsic factor antibody coated on the microparticles, whereby the microparticles are now coated with porcine intrinsic factor.

The loading of porcine intrinsic factor on the microparticles is determined by the designer of the assay, and the proper loading can readily be determined by one of ordinary skill in the art.

The nucleotide and amino acid sequences referred to in the specification are listed below:

List of Nucleotide and Amino Acid Sequence for the Porcine Intrinsic Factor cDNA Clones SEQ ID NO: 1 represents the nucleotide sequence of the Porcine IF cDNA$_{200-1254}$ (1054 bp)

```
5'-TACAACTTGAAGGCCCAGAAGCTCCTGACTTACAAGCTCATGGCTAC
CAACACCTCCGACCTGACCACAGGTCAGCTCGCCCTCACCATCATGGCAC
TCACCTCCTCCTGCCGAGACCCTGGGAACAGAATAGCCATTCTACAGGGG
CAAATGGAGAACTGGGCACCTCCAAGCCTTGATACCCATGCTTCAACCTT
CTACGAGCCAAGTCTGGGGATCCTGACGCTGTGCCAGAATAACCCGGAGA
AGACCTTACCGCTAGCAGCCCGTTTGCCAAGACCCTGCTGGCCAATTCCT
CTCCCTTCAACATGGACACAGGAGCAATGGCAACCTTGGCCCTGACCTGT
ATGTACAACAAGATCCCCGTAGGCTCAGAGGAAGGGTACAGAGCCCTGTT
CAGTCAGGTACTGAGGAATACTGTGGAGAATATCAGCATGAGGATCCAAG
ACAACGGAATCATTGGAAACATCTATAGCACTGGCCTCGCCATGCAGGCT
CTCTCTGTGACACCTGAGCAACCTAACAAGGAGTGGGACTGCCAGAAGAC
CATGGATACTGTACTTACTGAGATTAAGGAGGGGAAATTCCACAACCCCA
TGGCCATTGCCCAAATCCTCCCTTCCCTGAAAGGCAAGACCTATCTAGAT
GTGCCCCATGTGTCTTGCAGCCCTGGTCATGAGGTGCCACCAACTCTACC
CAACCACCCCAGCCCTGTTCCCACCCCAGCACCCAACATCACCGTCATAT
ACACCATAAATAACCAGCTGAGGGGCGTGGAGCTGCTCTTCAATGAAACC
ATCAGTGTTAGTGTGAAAAGAGGATCCGTGCTACTTATTGTCCTGGAGGA
GGCACAGCGCAAAAACCCCAAGTTCAAATTTGAAACGACAATGACGTCCT
GGGGACCGGTGGTCTCTTCTATTAACAATATCGCTGAAAATGTCAACCAC
AGGACGTACTGGCAGTTTCTGAGTGGCCAAACGCCCTTAAACGAAGGAGT
TGCGGACTATATACCCTTCAACCACGAGCACATCACAGCCAATTTCACAC
AGTACTAA-3'
```

SEQ ID NO: 2 represents the reverse complement of the nucleotide sequence of the Porcine IF cDNA$_{200-1254}$ (1054 bp)

```
5'-TTAGTACTGTGTGAAATTGGCTGTGATGTGCTCGTGGTTGAAGGGTA
TATAGTCCGCAACTCCTTCGTTTAAGGGCGTTTGGCCACTCAGAAACTGC
CAGTACGTCCTGTGGTTGACATTTTCAGCGATATTGTTAATAGAAGAGAC
CACCGGTCCCCAGGACGTCATTGTCGTTTCAAATTTGAACTTGGGGTTTT
TGCGCTGTGCCTCCTCCAGGACAATAAGTAGCACGGATCCTCTTTTCACA
CTAACACTGATGGTTTCATTGAAGAGCAGCTCCACGCCCCTCAGCTGGTT
ATTTATGGTGTATATGACGGTGATGTTGGGTGCTGGGGTGGGAACAGGGC
TGGGGTGGTTGGGTAGAGTTGGTGGCACCTCATGACCAGGGCTGCAAGAC
ACATGGGGCACATCTAGATAGGTCTTGCCTTTCAGGGAAGGGAGGATTTG
GGCAATGGCCATGGGGTTGTGGAATTTCCCCTCCTTAATCTCAGTAAGTA
CAGTATCCATGGTCTTCTGGCAGTCCCACTCCTTGTTAGGTTGCTCAGGT
GTCACAGAGAGAGCCTGCATGGCGAGGCCAGTGCTATAGATGTTTCCAAT
GATTCCGTTGTCTTGGATCCTCATGCTGATATTCTCCACAGTATTCCTCA
GTACCTGACTGAACAGGGCTCTGTACCCTTCCTCTGAGCCTACGGGGATC
TTGTTGTACATACAGGTCAGGGCCAAGGTTGCCATTGCTCCTGTGTCCAT
GTTGAAGGGAGAGGAATTGGCCAGCAGGGTCTTGGCAAAACGGGCTGCTA
GCGGTAAGGTCTTCTCCGGGTTATTCTGGCACAGCGTCAGGATCCCCAGA
CTTGGCTCGTAGAAGGTTGAAGCATGGGTATCAAGGCTTGGAGGTGCCCA
GTTCTCCATTTGCCCCTGTAGAATGGCTATTCTGTTCCCAGGGTCTCGGC
AGGAGGAGGTGAGTGCCATGATGGTGAGGGCGAGCTGACCTGTGGTCAGG
TCGGAGGTGTTGGTAGCCATGAGCTTGTAAGTCAGGAGCTTCTGGGCCTT
CAAGTTGTA-3'
```

SEQ ID NO: 3 represents the amino acid sequence of the Porcine IF cDNA$_{200-1254}$ (351 aa)

```
YNLKAQKLLTYKLMATNTSDLTTGQLALTIMALTSSCRDPGNRIAILQGQ
MENWAPPSLDTHASTFYEPSLGILTLCQNNPEKTLPLAARFAKTLLANSS
```

PFNMDTGAMATLALTCMYNKIPVGSEEGYRALFSQVLRNTVENISMRIQD

NGIIGNIYSTGLAMQALSVTPEQPNKEWDCQKTMDTVLTEIKEGKFHNPM

AIAQILPSLKGKTYLDVPHVSCSPGHEVPPTLPNHPSPVPTPAPNITVIY

TINNQLRGVELLFNETISVSVKRGSVLLIVLEEAQRKNPKFKFETTMTSW

GPVVSSINNIAENVNHRTYWQFLSGQTPLNEGVADYIPFNHEHITANFTQ

Y

SEQ ID NO: 4 represents the nucleotide sequence of the Porcine IF cDNA$_{14-1248}$ (1234 bp)

5'-CCTCTACCTCCTGAGCCTTCTCTGGGCTGTGGCCGGAACCAGCACCC

AGACCCGAAGCTCATGCTCTGTTCCCTCTGCAGAGCAGCCCTTGGTTAAT

GGCATCCAGGTGCTCATGGAGCAGTCCGTGACCAGCTCGGCCTTCCCAA

CCCCAGCATCCTGATTGCCATGAACCTGGCCGGAGCCTACAACACAGAGG

CCCAGGAGCTCCTGACTTACAAGCTCATGGCTACCAACACCTCCGACCTG

ACCACAGGTCAGCTCGCCCTCACCATCATGGCACTCACCTCCTCCTGCCG

AGACCCTGGGAACAGAATAGCCATTCTACAGGGGCAAATGGAGAACTGGG

CACCTCCAAGCCTTGATACCCATGCTTCAACCTTCTACGAGCCAAGTCTG

GGGATCCTGACGCTGTGCCAGAATAACCCGGAGAAGACCTTACCGCTAGC

AGCCCGTTTTGCCAAGACCCTGCTGGCCAATTCCTCTCCCTTCAACATGG

ACACAGGAGCAATGGCAACCTTGGCCCTGACCTGTATGTACAACAAGATC

CCCGTAGGCTCAGAGGAAGGGTACAGAGCCCTGTTCAGTCAGGTACTGAG

GAATACTGTGGAGAATATCAGCATGAGGATCCAAGACAACGGAATCATTG

GAAACATCTATAGCACTGGCCTCGCCATGCAGGCTCTCTCTGTGACACCT

GAGCAACCTAACAAGGAGTGGGACTGCCAGAAGACCATGGATACTGTACT

TACTGAGATTAAGGAGGGGAAATTCCACAACCCCATGGCCATTGCCCAAA

TCCTCCCTTCCCTGAAAGGCAAGACCTATCTAGATGTGCCCCATGTGTCT

TGCAGCCCTGGTCATGAGGTGCCACCAACTCTACCCAACCACCCCAGCCC

TGTTCCCACCCCAGCACCCAACATCACCGTCATATACACCATAAATAACC

AGCTGAGGGGCGTGGAGCTGCTCTTCAATGAAACCATCAGTGTTAGTGTG

AAAAGAGGATCCGTGCTACTTATTGTCCTGGAGGAGGCACAGCGCAAAAA

CCCCAAGTTCAAATTTGAAACGACAATGACGTCCTGGGGACCGGTGGTCT

CTTCTATTAACAATATCGCTGAAAATGTCAACCACAGGACGTACTGGCAG

TTTCTGAGTGGCCAAACGCCCTTAAACGAAGGAGTTGCGGACTATATACC

CTTCAACCACGAGCACATCACAGCCAATTTCACACAG-3'

SEQ ID NO: 5 represents the reverse complement of the nucleotide sequence of Porcine IF cDNA$_{14-1248}$ (1234 bp)

5'-CTGTGTGAAATTGGCTGTGATGTGCTCGTGGTTGAAGGGTATATAGT

CCGCAACTCCTTCGTTTAAGGGCGTTTGGCCACTCAGAAACTGCCAGTAC

GTCCTGTGGTTGACATTTTCAGCGATATTGTTAATAGAAGAGACCACCGG

TCCCCAGGACGTCATTGTCGTTTCAAATTTGAACTTGGGGTTTTTGCGCT

GTGCCTCCTCCAGGACAATAAGTAGCACGGATCCTCTTTTCACACTAACA

CTGATGGTTTCATTGAAGAGCAGCTCCACGCCCCTCAGCTGGTTATTTAT

GGTGTATATGACGGTGATGTTGGGTGCTGGGGTGGGAACAGGGCTGGGGT

GGTTGGGTAGAGTTGGTGGCACCTCATGACCAGGGCTGCAAGACACATGG

GGCACATCTAGATAGGTCTTGCCTTTCAGGGAAGGGAGGATTTGGGCAAT

GGCCATGGGGTTGTGGAATTTCCCCTCCTTAATCTCAGTAAGTACAGTAT

CCATGGTCTTCTGGCAGTCCCACTCCTTGTTAGGTTGCTCAGGTGTCACA

GAGAGAGCCTGCATGGCGAGGCCAGTGCTATAGATGTTTCCAATGATTCC

GTTGTCTTGGATCCTCATGCTGATATTCTCCACAGTATTCCTCAGTACCT

GACTGAACAGGGCTCTGTACCCTTCCTCTGAGCCTACGGGGATCTTGTTG

TACATACAGGTCAGGGCCAAGGTTGCCATTGCTCCTGTGTCCATGTTGAA

GGGAGAGGAATTGGCCAGCAGGGTCTTGGCAAAACGGGCTGCTAGCGGTA

AGGTCTTCTCCGGGTTATTCTGGCACAGCGTCAGGATCCCCAGACTTGGC

TCGTAGAAGGTTGAAGCATGGGTATCAAGGCTTGGAGGTGCCCAGTTCTC

CATTTGCCCCTGTAGAATGGCTATTCTGTTCCCAGGGTCTCGGCAGGAGG

AGGTGAGTGCCATGATGGTGAGGGCGAGCTGACCTGTGGTCAGGTCGGAG

GTGTTGGTAGCCATGAGCTTGTAAGTCAGGAGCTCCTGGGCCTCTGTGTT

GTAGGCTCCGGCCAGGTTCATGGCAATCAGGATGCTGGGGTTTGGGAAGG

CCGAGCTGGTCACGGACTGCTCCATGAGCACCTGGATGCCATTAACCAAG

GGCTGCTCTGCAGAGGGAACAGAGCATGAGCTTCGGGTCTGGGTGCTGGT

TCCGGCCACAGCCCAGAGAAGGCTCAGGAGGTAGAGG-3'

SEQ ID NO: 6 represents the amino acid sequence of the Porcine IF cDNA$_{14-1248}$ (411 aa)

LYLLSLLWAVAGTSTQTRSSCSVPSAEQPLVNGIQVLMEQSVTSSAFPNP

SILIAMNLAGAYNTEAQELLTYKLMATNTSDLTTGQLALTIMALTSSCRD

PGNRIAILQGQMENWAPPSLDTHASTFYEPSLGILTLCQNNPEKTLPLAA

RFAKTLLANSSPFNMDTGAMATLALTCMYNKIPVGSEEGYRALFSQVLRN

TVENISMRIQDNGIIGNIYSTGLAMQALSVTPEQPNKEWDCQKTMDTVLT

EIKEGKFHNPMAIAQILPSLKGKTYLDVPHVSCSPGHEVPPTLPNHPSPV

PTPAPNITVIYTINNQLRGVELLFNETISVSVKRGSVLLIVLEEAQRKNP

KFKFETTMTSWGPVVSSINNIAENVNHRTYWQFLSGQTPLNEGVADYIPF

NHEHITANFTQ

SEQ ID NO: 7 represents the nucleotide sequence of the Porcine IF cDNA$_{54-1254}$-Mature Peptide (1200 bp)

5'-AGCACCCAGACCCGAAGCTCATGCTCTGTTCCCTCTGCAGAGCAGCC

CTTGGTTAATGGCATCCAGGTGCTCATGGAGCAGTCCGTGACCAGCTCGG

CCTTCCCAAACCCCAGCATCCTGATTGCCATGAACCTGGCCGGAGCCTAC

AACACAGAGGCCCAGGAGCTCCTGACTTACAAGCTCATGGCTACCAACAC

-continued

CTCCGACCTGACCACAGGTCAGCTCGCCCTCACCATCATGGCACTCACCT

CCTCCTGCCGAGACCCTGGGAACAGAATAGCCATTCTACAGGGGCAAATG

GAGAACTGGGCACCTCCAAGCCTTGATACCCATGCTTCAACCTTCTACGA

GCCAAGTCTGGGGATCCTGACGCTGTGCCAGAATAACCCGGAGAAGACCT

TACCGCTAGCAGCCCGTTTTGCCAAGACCCTGCTGGCCAATTCCTCTCCC

TTCAACATGGACACAGGAGCAATGGCAACCTTGGCCCTGACCTGTATGTA

CAACAAGATCCCCGTAGGCTCAGAGGAAGGGTACAGAGCCCTGTTCAGTC

AGGTACTGAGGAATACTGTGGAGAATATCAGCATGAGGATCCAAGACAAC

GGAATCATTGGAAACATCTATAGCACTGGCCTCGCCATGCAGGCTCTCTC

TGTGACACCTGAGCAACCTAACAAGGAGTGGGACTGCCAGAAGACCATGG

ATACTGTACTTACTGAGATTAAGGAGGGGAAATTCCACAACCCCATGGCC

ATTGCCCAAATCCTCCCTTCCCTGAAAGGCAAGACCTATCTAGATGTGCC

CCATGTGTCTTGCAGCCCTGGTCATGAGGTGCCACCAACTCTACCCAACC

ACCCCAGCCCTGTTCCCACCCCAGCACCCAACATCACCGTCATATACACC

ATAAATAACCAGCTGAGGGGCGTGGAGCTGCTCTTCAATGAAACCATCAG

TGTTAGTGTGAAAAGAGGATCCGTGCTACTTATTGTCCTGGAGGAGGCAC

AGCGCAAAAACCCCAAGTTCAAATTTGAAACGACAATGACGTCCTGGGGA

CCGGTGGTCTCTTCTATTAACAATATCGCTGAAAATGTCAACCACAGGAC

GTACTGGCAGTTTCTGAGTGGCCAAACGCCCTTAAACGAAGGAGTTGCGG

ACTATATACCCTTCAACCACGAGCACATCACAGCCAATTTCACACAGTAC

TAA-3'

SEQ ID NO: 8 represents the reverse complement of the nucleotide sequence of the Porcine IF cDNA$_{54-1254}$-Mature Peptide (1200 bp)

5'-TTAGTACTGTGTGAAATTGGCTGTGATGTGCTCGTGGTTGAAGGGTA

TATAGTCCGCAACTCCTTCGTTTAAGGGCGTTTGGCCACTCAGAAACTGC

CAGTACGTCCTGTGGTTGACATTTTCAGCGATATTGTTAATAGAAGAGAC

CACCGGTCCCCAGGACGTCATTGTCGTTTCAAATTTGAACTTGGGGTTTT

TGCGCTGTGCCTCCTCCAGGACAATAAGTAGCACGGATCCTCTTTTCACA

CTAACACTGATGGTTTCATTGAAGAGCAGCTCCACGCCCCTCAGCTGGTT

ATTTATGGTGTATATGACGGTGATGTTGGGTGCTGGGGTGGGAACAGGGC

TGGGGTGGTTGGGTAGAGTTGGTGGCACCTCATGACCAGGGCTGCAAGAC

ACATGGGGCACATCTAGATAGGTCTTGCCTTTCAGGGAAGGGAGGATTTG

GGCAATGGCCATGGGGTTGTGGAATTTCCCCTCCTTAATCTCAGTAAGTA

CAGTATCCATGGTCTTCTGGCAGTCCCACTCCTTGTTAGGTTGCTCAGGT

GTCACAGAGAGAGCCTGCATGGCGAGGCCAGTGCTATAGATGTTTCCAAT

GATTCCGTTGTCTTGGATCCTCATGCTGATATTCTCCACAGTATTCCTCA

GTACCTGACTGAACAGGGCTCTGTACCCTTCCTCTGAGCCTACGGGGATC

TTGTTGTACATACAGGTCAGGGCCAAGGTTGCCATTGCTCCTGTGTCCAT

GTTGAAGGGAGAGGAATTGGCCAGCAGGGTCTTGGCAAAACGGGCTGCTA

GCGGTAAGGTCTTCTCCGGGTTATTCTGGCACAGCGTCAGGATCCCCAGA

CTTGGCTCGTAGAAGGTTGAAGCATGGGTATCAAGGCTTGGAGGTGCCCA

GTTCTCCATTTGCCCCTGTAGAATGGCTATTCTGTTCCCAGGGTCTCGGC

AGGAGGAGGTGAGTGCCATGATGGTGAGGGCGAGCTGACCTGTGGTCAGG

TCGGAGGTGTTGGTAGCCATGAGCTTGTAAGTCAGGAGCTCCTGGGCCTC

TGTGTTGTAGGCTCCGGCCAGGTTCATGGCAATCAGGATGCTGGGGTTTG

GGAAGGCCGAGCTGGTCACGGACTGCTCCATGAGCACCTGGATGCCATTA

ACCAAGGGCTGCTCTGCAGAGGGAACAGAGCATGAGCTTCGGGTCTGGGT

GCT-3'

SEQ ID NO: 9 represents the amino acid sequence of the Porcine IF cDNA$_{54-1254}$-Mature Peptide (399 aa)

STQTRSSCSVPSAEQPLVNGIQVLMEQSVTSSAFPNPSILIAMNLAGAYN

TEAQELLTYKLMATNTSDLTTGQLALTIMALTSSCRDPGNRIAILQGQME

NWAPPSLDTHASTFYEPSLGILTLCQNNPEKTLPLAARFAKTLLANSSPF

NMDTGAMATLALTCMYNKIPVGSEEGYRALFSQVLRNTVENISMRIQDNG

IIGNIYSTGLAMQALSVTPEQPNKEWDCQKTMDTVLTEIKEGKFHNPMAI

AQILPSLKGKTYLDVPHVSCSPGHEVPPTLPNHPSPVPTPAPNITVIYTI

NNQLRGVELLFNETISVSVKRGSVLLIVLEEAQRKNPKFKFETTMTSWGP

VVSSINNIAENVNHRTYWQFLSGQTPLNEGVADYIPFNHEHITANFTQY

SEQ ID NO: 10 represents the nucleotide sequence of the Forward Primer huIF200For (30 nt)

5'- TACAACTTGAAGGCCCAGAAGCTCCTGACT -3'

SEQ ID NO: 11 represents the nucleotide sequence of the Reverse Primer huIF Reverse 1 (33 nt)

5'-TTAGTACTGTGTGAAATTGGCTGTGATGTGCTC-3'

SEQ ID NO: 12 represents the nucleotide sequence of the Forward Primer huIF-For14 (29 nt)

5'-CCCTCTACCTCCTGAGCCTTCTCTGGGCT-3'

SEQ ID NO: 13 represents the nucleotide sequence of the Reverse Primer huIF 1248Rev (25 nt)

5'-CTGTGTGAAATTGGCTGTGATGTGC-3'

SEQ ID NO: 14 represents the nucleotide sequence of the Forward Primer pIFMP-ForI (39 nt)

5'-ATACAGAATTCATGAGCACCCAGACCCGAAGCTCATGCT-3'

SEQ ID NO: 15 represents the nucleotide sequence of the Reverse Primer pIFMP-RevXhoI (44 nt)

5'-GATACCTCGAGTTAGTACTGTGTGAAATTGGCTGTGATGTGCTC-3'

SEQ ID NO: 16 represents the nucleotide sequence of the Forward Primer pIF-PIC-MP-For EcoRI (36 nt)

5'-ATACAGAATTCAGCACCCAGACCCGAAGCTCATGCT-3'

SEQ ID NO: 17 represents the nucleotide sequence of the Reverse Primer pIF-MP-pMAL-SalI Rev primer (44 nt)

5'-GATATGTCGACTTAGTACTGTGTGAAATTGGCTGTGATGTGCTC-3'

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A method for determining the quantity of vitamin $B_{12}$ in a biological sample, said method comprising the steps of:
    (a) combining said biological sample with paramagnetic microparticles coated with a purified recombinant porcine intrinsic factor, wherein the amino acid sequence of said porcine intrinsic factor is identical to an amino acid sequence comprising SEQ ID NO: 3;
    (b) allowing vitamin $B_{12}$ present in said sample to bind to said paramagnetic microparticles coated with said porcine intrinsic factor;
    (c) adding conjugate capable of undergoing chemiluminescent reaction to said mixture of step (b);
    (d) causing said chemiluminescent reaction to occur; and
    (e) measuring the resulting chemiluminescent reaction as relative light units to determine the quantity of vitamin $B_{12}$ in said biological sample.

2. A method for determining the quantity of vitamin $B_{12}$ in a biological sample, said method comprising the steps of:
    (a) combining said biological sample with at least one pre-treatment reagent;
    (b) combining said pre-treated sample of step (a) with paramagnetic microparticles coated with a purified recombinant porcine intrinsic factor, wherein the amino acid sequence of said porcine intrinsic factor is identical to an amino acid sequence comprising SEQ ID NO: 3;
    (c) allowing vitamin $B_{12}$ present in said sample to bind to said paramagnetic microparticles coated with said porcine intrinsic factor;
    (d) washing said mixture of step (c);
    (e) adding conjugate capable of undergoing chemiluminescent reaction to said washed mixture of step (d);
    (f) adding pre-trigger and trigger solutions to said reaction mixture of step (e) to cause said chemiluminescent reaction to occur; and
    (g) measuring the resulting chemiluminescent reaction as relative light units to determine the quantity of vitamin $B_{12}$ in said biological sample.

3. A method for determining the quantity of vitamin $B_{12}$ in a biological sample, said method comprising the steps of:
    (a) combining said biological sample with paramagnetic microparticles coated with a purified recombinant porcine intrinsic factor comprising the amino acid sequence SEQ ID NO: 3, wherein said purified recombinant porcine intrinsic factor is encoded by a nucleotide sequence identical to the nucleotide sequence SEQ ID NO: 1;
    (b) allowing vitamin $B_{12}$ present in said sample to bind to said paramagnetic microparticles coated with said porcine intrinsic factor;
    (c) adding conjugate capable of undergoing chemiluminescent reaction to said mixture of step (b);
    (d) causing said chemiluminescent reaction to occur; and
    (e) measuring the resulting chemiluminescent reaction as relative light units to determine the quantity of vitamin $B_{12}$ in said biological sample.

4. A method for determining the quantity of vitamin $B_{12}$ in a biological sample, said method comprising the steps of:
    (a) combining said biological sample with at least one pre-treatment reagent;
    (b) combining said pre-treated sample of step (a) with paramagnetic microparticles coated with a purified recombinant porcine intrinsic factor comprising the amino acid sequence SEQ ID NO: 3, wherein said purified recombinant porcine intrinsic factor is encoded by a nucleotide sequence identical to the nucleotide sequence SEQ ID NO: 1;
    (c) allowing vitamin $B_{12}$ present in said sample to bind to said paramagnetic microparticles coated with said porcine intrinsic factor;
    (d) washing said mixture of step (c);
    (e) adding conjugate capable of undergoing chemiluminescent reaction to said washed mixture of step (d);
    (f) adding pre-trigger and trigger solutions to said reaction mixture of step (e) to cause said chemiluminescent reaction to occur; and
    (g) measuring the resulting chemiluminescent reaction as relative light units to determine the quantity of vitamin $B_{12}$ in said biological sample.

* * * * *

SEQUENCE LISTING

```
<160> NUMBER OF SEQ ID NOS: 27

<210> SEQ ID NO 1
<211> LENGTH: 1056
<212> TYPE: DNA
<213> ORGANISM: S. scrofa

<400> SEQUENCE: 1
tacaacttga aggcccagaa gctcctgact tacaagctca tggctaccaa cacctccgac      60
ctgaccacag gtcagctcgc cctcaccatc atggcactca cctcctcctg ccgagaccct     120
gggaacagaa tagccattct acaggggcaa atggagaact gggcacctcc aagcttgat     180 acccatgctt caaccttcta cgagccaagt ctggggatcc tgacgctgtg ccagaataac     240
ccggagaaga ccttaccgct agcagcccgt tttgccaaga ccctgctggc caattcctct     300
cccttcaaca tggacacagg agcaatggca accttggccc tgacctgtat gtacaacaag     360
atccccgtag gctcagagga agggtacaga gccctgttca gtcaggtact gaggaatact     420
gtggagaata tcagcatgag gatccaagac aacggaatca ttggaaacat ctatagcact     480
ggcctcgcca tgcaggctct ctctgtgaca cctgagcaac ctaacaagga gtgggactgc     540
cagaagacca tggatactgt acttactgag attaaggagg ggaaattcca caaccccatg     600
gccattgccc aaatcctccc ttccctgaaa ggcaagacct atctagatgt gccccatgtg     660
tcttgcagcc ctggtcatga ggtgccacca actctaccca accaccccag ccctgttccc     720
accccagcac ccaacatcac cgtcatatac accataaata accagctgag gggcgtggag     780
ctgctcttca atgaaaccat cagtgttagt gtgaaaagag gatccgtgct acttattgtc     840
ctggaggagg cacagcgcaa aaaccccaag ttcaaatttg aaacgacaat gacgtcctgg     900
ggaccggtgg tctcttctat taacaatatc gctgaaaatg tcaaccacag gacgtactgg     960
cagtttctga gtggccaaac gcccttaaac gaaggagttg cggactatat accecttcaac    1020 cacgagcaca tcacagccaa tttcacacag tactaa                               1056

<210> SEQ ID NO 2
<211> LENGTH: 1056
<212> TYPE: DNA
<213> ORGANISM: S. scrofa

<400> SEQUENCE: 2
ttagtactgt gtgaaattgg ctgtgatgtg ctcgtggttg aagggtatat agtccgcaac      60
tccttcgttt aagggcgttt ggccactcag aaactgccag tacgtcctgt ggttgacatt     120
ttcagcgata ttgttaatag aagagaccac cggtccccag gacgtcattg tcgtttcaaa     180
tttgaacttg gggttttttgc gctgtgcctc ctccaggaca ataagtagca cggatcctct     240
```

```
tttcacacta acactgatgg tttcattgaa gagcagctcc acgcccctca gctggttatt    300
tatggtgtat atgacggtga tgttgggtgc tggggtggga acagggctgg ggtggttggg    360
tagagttggt ggcacctcat gaccagggct gcaagacaca tggggcacat ctagataggt    420
cttgcctttc agggaaggga ggatttgggc aatggccatg gggttgtgga atttcccctc    480
cttaatctca gtaagtacag tatccatggt cttctggcag tcccactcct tgttaggttg    540
ctcaggtgtc acagagagag cctgcatggc gaggccagtg ctatagatgt ttccaatgat    600
tccgttgtct tggatcctca tgctgatatt ctccacagta ttcctcagta cctgactgaa    660
cagggctctg taccttcct ctgagcctac ggggatcttg ttgtacatac aggtcagggc    720
caaggttgcc attgctcctg tgtccatgtt gaagggagag gaattggcca gcagggtctt    780
ggcaaaacgg gctgctagcg gtaaggtctt ctccgggtta ttctggcaca gcgtcaggat    840
ccccagactt ggctcgtaga aggttgaagc atgggtatca aggcttggag gtgcccagtt    900
ctccatttgc ccctgtagaa tggctattct gttcccaggg tctcggcagg aggaggtgag    960
tgccatgatg gtgagggcga gctgacctgt ggtcaggtcg gaggtgttgg tagccatgag   1020
cttgtaagtc aggagcttct gggccttcaa gttgta                             1056
```

<210> SEQ ID NO 3
<211> LENGTH: 351
<212> TYPE: PRT
<213> ORGANISM: S. scrofa

<400> SEQUENCE: 3

```
Tyr Asn Leu Lys Ala Gln Lys Leu Leu Thr Tyr Lys Leu Met Ala Thr
1               5                   10                  15

Asn Thr Ser Asp Leu Thr Thr Gly Gln Leu Ala Leu Thr Ile Met Ala
            20                  25                  30

Leu Thr Ser Ser Cys Arg Asp Pro Gly Asn Arg Ile Ala Ile Leu Gln
        35                  40                  45

Gly Gln Met Glu Asn Trp Ala Pro Pro Ser Leu Asp Thr His Ala Ser
    50                  55                  60

Thr Phe Tyr Glu Pro Ser Leu Gly Ile Leu Thr Leu Cys Gln Asn Asn
65                  70                  75                  80

Pro Glu Lys Thr Leu Pro Leu Ala Ala Arg Phe Ala Lys Thr Leu Leu
                85                  90                  95

Ala Asn Ser Ser Pro Phe Asn Met Asp Thr Gly Ala Met Ala Thr Leu
            100                 105                 110

Ala Leu Thr Cys Met Tyr Asn Lys Ile Pro Val Gly Ser Glu Glu Gly
        115                 120                 125

Tyr Arg Ala Leu Phe Ser Gln Val Leu Arg Asn Thr Val Glu Asn Ile
    130                 135                 140

Ser Met Arg Ile Gln Asp Asn Gly Ile Ile Gly Asn Ile Tyr Ser Thr
145                 150                 155                 160

Gly Leu Ala Met Gln Ala Leu Ser Val Thr Pro Glu Gln Pro Asn Lys
                165                 170                 175

Glu Trp Asp Cys Gln Lys Thr Met Asp Thr Val Leu Thr Glu Ile Lys
            180                 185                 190

Glu Gly Lys Phe His Asn Pro Met Ala Ile Ala Gln Ile Leu Pro Ser
        195                 200                 205

Leu Lys Gly Lys Thr Tyr Leu Asp Val Pro His Val Ser Cys Ser Pro
    210                 215                 220
```

```
Gly His Glu Val Pro Pro Thr Leu Pro Asn His Pro Ser Pro Val Pro
225                 230                 235                 240

Thr Pro Ala Pro Asn Ile Thr Val Ile Tyr Thr Ile Asn Asn Gln Leu
            245                 250                 255

Arg Gly Val Glu Leu Leu Phe Asn Glu Thr Ile Ser Val Ser Val Lys
        260                 265                 270

Arg Gly Ser Val Leu Leu Ile Val Leu Glu Glu Ala Gln Arg Lys Asn
    275                 280                 285

Pro Lys Phe Lys Phe Glu Thr Thr Met Thr Ser Trp Gly Pro Val Val
290                 295                 300

Ser Ser Ile Asn Asn Ile Ala Glu Asn Val Asn His Arg Thr Tyr Trp
305                 310                 315                 320

Gln Phe Leu Ser Gly Gln Thr Pro Leu Asn Glu Gly Val Ala Asp Tyr
            325                 330                 335

Ile Pro Phe Asn His Glu His Ile Thr Ala Asn Phe Thr Gln Tyr
            340                 345                 350

<210> SEQ ID NO 4
<211> LENGTH: 1232
<212> TYPE: DNA
<213> ORGANISM: S. scrofa

<400> SEQUENCE: 4
cctctacctc ctgagccttc tctgggctgt ggccggaacc agcacccaga cccgaagctc      60
atgctctgtt ccctctgcag agcagccctt ggttaatggc atccaggtgc tcatggagca    120
gtccgtgacc agctcggcct cccaaaaccc cagcatcctg attgccatga acctggccgg    180
agcctacaac acagaggccc aggagctcct gacttacaag ctcatggcta ccaacacctc    240
cgacctgacc acaggtcagc tcgccctcac catcatggca ctcacctcct cctgccgaga    300
ccctgggaac agaatagcca ttctacaggg gcaaatggag aactgggcac tccaagcct    360 tgatacccat gcttcaacct ctacgagcc aagtctgggg atcctgacgc tgtgccagaa    420
taacccggag aagaccttac cgctagcagc ccgttttgcc aagaccctgc tggccaattc    480
ctctcccttc aacatggaca caggagcaat ggcaaccttg ccctgacct gtatgtacaa    540 caagatcccc gtaggctcag aggaagggta cagagccctg ttcagtcagg tactgaggaa    600
tactgtggag aatatcagca tgaggatcca agacaacgga atcattggaa acatctatag    660
cactggcctc gccatgcagg ctctctctgt gacacctgag caacctaaca aggagtggga    720
ctgccagaag accatggata ctgtacttac tgagattaag gaggggaaat tccacaaccc    780
catggccatt gcccaaatcc tcccttccct gaaaggcaag acctatctag atgtgcccca    840
tgtgtcttgc agccctggtc atgaggtgcc accaactcta cccaaccacc ccagccctgt    900 tcccaccca gcacccaaca tcaccgtcat atacaccata ataaccagc tgaggggcgt    960 ggagctgctc ttcaatgaaa ccatcagtgt tagtgtgaaa agaggatccg tgctacttat    1020
tgtcctggag gaggcacagc gcaaaaccc caagttcaaa tttgaaacga caatgacgtc    1080
ctggggaccg gtggtctctt ctattaacaa tatcgctgaa aatgtcaacc acaggacgta    1140
ctggcagttt ctgagtggcc aaacgcccct aaacgaagga gttgcggact ataccctt    1200 caaccacgag cacatcacag ccaatttcac ac                                  1232

<210> SEQ ID NO 5
<211> LENGTH: 1232
<212> TYPE: DNA
<213> ORGANISM: S. scrofa
```

<400> SEQUENCE: 5

```
ctgtgtgaaa ttggctgtga tgtgctcgtg gttgaagggt atatagtccg caactccttc      60
gtttaagggc gtttggccac tcagaaactg ccagtacgtc ctgtggttga cattttcagc     120
gatattgtta atagaagaga ccaccggtcc ccaggacgtc attgtcgttt caaatttgaa     180
cttggggttt ttgcgctgtg cctcctccag acaataagt agcacggatc tctttttcac      240
actaacactg atggtttcat tgaagagcag ctccacgccc ctcagctggt tatttatggt     300
gtatatgacg tgatgttgg gtgctgggggt gggaacaggg ctgggtggt tgggtagagt      360
tggtggcacc tcatgaccag ggctgcaaga cacatggggc acatctagat aggtcttgcc     420
tttcagggaa gggaggattt gggcaatggc catggggttg tggaatttcc cctccttaat     480
ctcagtaagt acagtatcca tggtcttctg gcagtcccac tccttgttag gttgctcagg     540
tgtcacagag agagcctgca tggcgaggcc agtgctatag atgtttccaa tgattccgtt     600
gtcttggatc ctcatgctga tattctccac agtattcctc agtacctgac tgaacagggc     660
tctgtaccct cctctgagc ctacgggat cttgttgtac atacaggtca gggccaaggt       720
tgccattgct cctgtgtcca tgttgaaggg agaggaattg ccagcaggg tcttggcaaa      780
acgggctgct agcggtaagg tcttctccgg gttattctgg cacagcgtca ggatccccag     840
acttggctcg tagaaggttg aagcatgggt atcaaggctt ggaggtgccc agttctccat     900
ttgcccctgt agaatggcta ttctgttccc agggtctcgg caggaggagg tgagtgccat     960
gatggtgagg gcgagctgac ctgtggtcag gtcggaggtg ttggtagcca tgagcttgta    1020
agtcaggagc tcctgggcct ctgtgttgta ggctccggcc aggttcatgg caatcaggat    1080
gctgggtttt gggaaggccg agctggtcac ggactgctcc atgagcacct ggatgccatt    1140
aaccaagggc tgctctgcag agggaacaga gcatgagctt cgggtctggg tgctggttcc    1200
ggccacagcc cagagaaggc tcaggaggta ga                                  1232
```

<210> SEQ ID NO 6
<211> LENGTH: 411
<212> TYPE: PRT
<213> ORGANISM: S. scrofa

<400> SEQUENCE: 6

```
Leu Tyr Leu Leu Ser Leu Leu Trp Ala Val Ala Gly Thr Ser Thr Gln
1               5                   10                  15

Thr Arg Ser Ser Cys Ser Val Pro Ser Ala Glu Gln Pro Leu Val Asn
            20                  25                  30

Gly Ile Gln Val Leu Met Glu Gln Ser Val Thr Ser Ser Ala Phe Pro
        35                  40                  45

Asn Pro Ser Ile Leu Ile Ala Met Asn Leu Ala Gly Ala Tyr Asn Thr
    50                  55                  60

Glu Ala Gln Glu Leu Leu Thr Tyr Lys Leu Met Ala Thr Asn Thr Ser
65                  70                  75                  80

Asp Leu Thr Thr Gly Gln Leu Ala Leu Thr Ile Met Ala Leu Thr Ser
                85                  90                  95

Ser Cys Arg Asp Pro Gly Asn Arg Ile Ala Ile Leu Gln Gly Gln Met
            100                 105                 110

Glu Asn Trp Ala Pro Pro Ser Leu Asp Thr His Ala Ser Thr Phe Tyr
        115                 120                 125

Glu Pro Ser Leu Gly Ile Leu Thr Leu Cys Gln Asn Asn Pro Glu Lys
    130                 135                 140
```

```
Thr Leu Pro Leu Ala Ala Arg Phe Ala Lys Thr Leu Leu Ala Asn Ser
145                 150                 155                 160

Ser Pro Phe Asn Met Asp Thr Gly Ala Met Ala Thr Leu Ala Leu Thr
                165                 170                 175

Cys Met Tyr Asn Lys Ile Pro Val Gly Ser Glu Glu Gly Tyr Arg Ala
            180                 185                 190

Leu Phe Ser Gln Val Leu Arg Asn Thr Val Glu Asn Ile Ser Met Arg
        195                 200                 205

Ile Gln Asp Asn Gly Ile Ile Gly Asn Ile Tyr Ser Thr Gly Leu Ala
210                 215                 220

Met Gln Ala Leu Ser Val Thr Pro Glu Gln Pro Asn Lys Glu Trp Asp
225                 230                 235                 240

Cys Gln Lys Thr Met Asp Thr Val Leu Thr Glu Ile Lys Glu Gly Lys
                245                 250                 255

Phe His Asn Pro Met Ala Ile Ala Gln Ile Leu Pro Ser Leu Lys Gly
            260                 265                 270

Lys Thr Tyr Leu Asp Val Pro His Val Ser Cys Ser Pro Gly His Glu
        275                 280                 285

Val Pro Pro Thr Leu Pro Asn His Pro Ser Pro Val Pro Thr Pro Ala
290                 295                 300

Pro Asn Ile Thr Val Ile Tyr Thr Ile Asn Asn Gln Leu Arg Gly Val
305                 310                 315                 320

Glu Leu Leu Phe Asn Glu Thr Ile Ser Val Ser Val Lys Arg Gly Ser
                325                 330                 335

Val Leu Leu Ile Val Leu Glu Glu Ala Gln Arg Lys Asn Pro Lys Phe
            340                 345                 350

Lys Phe Glu Thr Thr Met Thr Ser Trp Gly Pro Val Ser Ser Ile
        355                 360                 365

Asn Asn Ile Ala Glu Asn Val Asn His Arg Thr Tyr Trp Gln Phe Leu
370                 375                 380

Ser Gly Gln Thr Pro Leu Asn Glu Gly Val Ala Asp Tyr Ile Pro Phe
385                 390                 395                 400

Asn His Glu His Ile Thr Ala Asn Phe Thr Gln
                405                 410

<210> SEQ ID NO 7
<211> LENGTH: 1200
<212> TYPE: DNA
<213> ORGANISM: S. scrofa

<400> SEQUENCE: 7
agcacccaga cccgaagctc atgctctgtt ccctctgcag agcagccctt ggttaatggc      60
atccaggtgc tcatggagca gtccgtgacc agctcggcct cccaaaccc cagcatcctg     120 attgccatga acctggccgg agcctacaac acagaggccc aggagctcct gacttacaag     180
ctcatggcta ccaacacctc cgacctgacc acaggtcagc tcgccctcac catcatggca     240
ctcacctcct cctgccgaga ccctgggaac agaatagcca ttctacaggg gcaaatggag     300
aactgggcac ctccaagcct tgatacccat gcttcaacct tctacgagcc aagtctgggg     360
atcctgacgc tgtgccagaa taacccggag aagaccttac cgctagcagc ccgttttgcc     420
aagaccctgc tggccaattc ctctcccttc aacatggaca caggagcaat ggcaaccttg     480
gccctgacct gtatgtacaa caagatcccc gtaggctcag aggaagggta cagagccctg     540
ttcagtcagg tactgaggaa tactgtggag aatatcagca tgaggatcca agacaacgga     600
```

```
atcattggaa acatctatag cactggcctc gccatgcagg ctctctctgt gacacctgag    660
caacctaaca aggagtggga ctgccagaag accatggata ctgtacttac tgagattaag    720 gagggaaat tccacaaccc catggccatt gcccaaatcc tcccttccct gaaaggcaag     780
acctatctag atgtgcccca tgtgtcttgc agccctggtc atgaggtgcc accaactcta    840
cccaaccacc ccagccctgt tcccacccca gcacccaaca tcaccgtcat atacaccata    900
aataaccagc tgagggcgt ggagctgctc ttcaatgaaa ccatcagtgt tagtgtgaaa     960
agaggatccg tgctacttat tgtcctggag gaggcacagc gcaaaaaccc caagttcaaa   1020
tttgaaacga caatgacgtc ctggggaccg tggtctctt ctattaacaa tatcgctgaa    1080
aatgtcaacc acaggacgta ctggcagttt ctgagtggcc aaacgccctt aaacgaagga   1140
gttgcggact atatacccct caaccacgag cacatcacag ccaatttcac acagtactaa   1200
```

<210> SEQ ID NO 8
<211> LENGTH: 1200
<212> TYPE: DNA
<213> ORGANISM: S. scrofa

<400> SEQUENCE: 8

```
ttagtactgt gtgaaattgg ctgtgatgtg ctcgtggttg aagggtatat agtccgcaac     60
tccttcgttt aagggcgttt ggccactcag aaactgccag tacgtcctgt ggttgacatt    120
ttcagcgata ttgttaatag aagagaccac cggtccccag acgtcattg tcgtttcaaa    180 tttgaacttg gggttttttgc gctgtgcctc tccaggaca ataagtagca cggatcctct    240
tttcacacta acactgatgg tttcattgaa gagcagctcc acgcccctca gctggttatt    300
tatggtgtat atgacggtga tgttgggtgc tggggtggga acagggctgg ggtggttggg    360
tagagttggt ggcacctcat gaccagggct gcaagacaca tggggcacat ctagataggt    420
cttgcctttc agggaaggga ggatttgggc aatggccatg gggttgtgga atttcccctc    480
cttaatctca gtaagtacag tatccatggt cttctggcag tcccactcct tgttaggttg    540
ctcaggtgtc acagagagag cctgcatggc gaggccagtg ctatagatgt ttccaatgat    600
tccgttgtct tggatcctca tgctgatatt ctccacagta ttcctcagta cctgactgaa    660
cagggctctg tacccttcct ctgagcctac ggggatcttg ttgtacatac aggtcagggc    720
caaggttgcc attgctcctg tgtccatgtt gaagggagag gaattggcca gcagggtctt    780
ggcaaaacgg gctgctagcg gtaaggtctt ctccgggtta ttctggcaca gcgtcaggat    840
ccccagactt ggctcgtaga aggttgaagc atgggtatca aggcttggag gtgcccagtt    900
ctccatttgc ccctgtagaa tggctattct gttcccaggg tctcggcagg aggaggtgag    960
tgccatgatg gtgagggcga gctgacctgt ggtcaggtcg gaggtgttgg tagccatgag   1020
cttgtaagtc aggagctcct gggctctgt gttgtaggct ccggccaggt tcatggcaat    1080
caggatgctg gggtttggga aggccgagct ggtcacggac tgctccatga gcacctggat   1140
gccattaacc aagggctgct ctgcagaggg aacagagcat gagcttcggg tctgggtgct   1200
```

<210> SEQ ID NO 9
<211> LENGTH: 399
<212> TYPE: PRT
<213> ORGANISM: S. scrofa

<400> SEQUENCE: 9

```
Ser Thr Gln Thr Arg Ser Ser Cys Ser Val Pro Ser Ala Glu Gln Pro
1               5                   10                  15
```

```
Leu Val Asn Gly Ile Gln Val Leu Met Glu Gln Ser Val Thr Ser Ser
             20                  25                  30

Ala Phe Pro Asn Pro Ser Ile Leu Ile Ala Met Asn Leu Ala Gly Ala
             35                  40                  45

Tyr Asn Thr Glu Ala Gln Glu Leu Leu Thr Tyr Lys Leu Met Ala Thr
             50                  55                  60

Asn Thr Ser Asp Leu Thr Thr Gly Gln Leu Ala Leu Thr Ile Met Ala
 65                  70                  75                  80

Leu Thr Ser Ser Cys Arg Asp Pro Gly Asn Arg Ile Ala Ile Leu Gln
                 85                  90                  95

Gly Gln Met Glu Asn Trp Ala Pro Pro Ser Leu Asp Thr His Ala Ser
            100                 105                 110

Thr Phe Tyr Glu Pro Ser Leu Gly Ile Leu Thr Leu Cys Gln Asn Asn
            115                 120                 125

Pro Glu Lys Thr Leu Pro Leu Ala Ala Arg Phe Ala Lys Thr Leu Leu
            130                 135                 140

Ala Asn Ser Ser Pro Phe Asn Met Asp Thr Gly Ala Met Ala Thr Leu
145                 150                 155                 160

Ala Leu Thr Cys Met Tyr Asn Lys Ile Pro Val Gly Ser Glu Glu Gly
                165                 170                 175

Tyr Arg Ala Leu Phe Ser Gln Val Leu Arg Asn Thr Val Glu Asn Ile
            180                 185                 190

Ser Met Arg Ile Gln Asp Asn Gly Ile Gly Asn Ile Tyr Ser Thr
            195                 200                 205

Gly Leu Ala Met Gln Ala Leu Ser Val Thr Pro Glu Gln Pro Asn Lys
            210                 215                 220

Glu Trp Asp Cys Gln Lys Thr Met Asp Thr Val Leu Thr Glu Ile Lys
225                 230                 235                 240

Glu Gly Lys Phe His Asn Pro Met Ala Ile Ala Gln Ile Leu Pro Ser
                245                 250                 255

Leu Lys Gly Lys Thr Tyr Leu Asp Val Pro His Val Ser Cys Ser Pro
            260                 265                 270

Gly His Glu Val Pro Pro Thr Leu Pro Asn His Pro Ser Pro Val Pro
            275                 280                 285

Thr Pro Ala Pro Asn Ile Thr Val Ile Tyr Thr Ile Asn Asn Gln Leu
            290                 295                 300

Arg Gly Val Glu Leu Leu Phe Asn Glu Thr Ile Ser Val Ser Val Lys
305                 310                 315                 320

Arg Gly Ser Val Leu Leu Ile Val Leu Glu Glu Ala Gln Arg Lys Asn
                325                 330                 335

Pro Lys Phe Lys Phe Glu Thr Thr Met Thr Ser Trp Gly Pro Val Val
            340                 345                 350

Ser Ser Ile Asn Asn Ile Ala Glu Asn Val Asn His Arg Thr Tyr Trp
            355                 360                 365

Gln Phe Leu Ser Gly Gln Thr Pro Leu Asn Glu Gly Val Ala Asp Tyr
            370                 375                 380

Ile Pro Phe Asn His Glu His Ile Thr Ala Asn Phe Thr Gln Tyr
385                 390                 395

<210> SEQ ID NO 10
<211> LENGTH: 30
<212> TYPE: DNA
<213> ORGANISM: Artificial sequence
<220> FEATURE:
```

<223> OTHER INFORMATION: Chemically synthesized - Forward Primer
huIF200For

<400> SEQUENCE: 10
tacaacttga aggcccagaa gctcctgact                                    30

<210> SEQ ID NO 11
<211> LENGTH: 33
<212> TYPE: DNA
<213> ORGANISM: Artificial sequence
<220> FEATURE:
<223> OTHER INFORMATION: Chemically synthesized - Reverse Primer huIF
Reverse 1

<400> SEQUENCE: 11
ttagtactgt gtgaaattgg ctgtgatgtg ctc                                33

<210> SEQ ID NO 12
<211> LENGTH: 29
<212> TYPE: DNA
<213> ORGANISM: Artificial sequence
<220> FEATURE:
<223> OTHER INFORMATION: Chemically synthesized - Forward Primer
huIF-For14

<400> SEQUENCE: 12
ccctctacct cctgagcctt tctctgggct                                    29

<210> SEQ ID NO 13
<211> LENGTH: 25
<212> TYPE: DNA
<213> ORGANISM: Artificial sequence
<220> FEATURE:
<223> OTHER INFORMATION: Chemically synthesized - Reverse Primer huIF
1248Rev

<400> SEQUENCE: 13
ctgtgtgaaa ttggctgtga tgtgc                                         25

<210> SEQ ID NO 14
<211> LENGTH: 39
<212> TYPE: DNA
<213> ORGANISM: Artificial sequence
<220> FEATURE:
<223> OTHER INFORMATION: Chemically synthesized - Forward Primer
pIFMP-ForI

<400> SEQUENCE: 14
atacagaatt catgagcacc cagacccgaa gctcatgct                          39

<210> SEQ ID NO 15
<211> LENGTH: 44
<212> TYPE: DNA
<213> ORGANISM: Artificial sequence
<220> FEATURE:
<223> OTHER INFORMATION: Chemically synthesized - Reverse Primer
pIFMP-RevXhoI

<400> SEQUENCE: 15
gatacctcga gttagtactg tgtgaaattg ctgtgatgt gctc                     44

<210> SEQ ID NO 16
<211> LENGTH: 36
<212> TYPE: DNA
<213> ORGANISM: Artificial sequence
<220> FEATURE:
<223> OTHER INFORMATION: Chemically synthesized - Forward Primer pIF-PIC-MP-For EcoRI

<400> SEQUENCE: 16
atacagaatt cagcacccag acccgaagct catgct                                          36

<210> SEQ ID NO 17
<211> LENGTH: 44
<212> TYPE: DNA
<213> ORGANISM: Artificial sequence
<220> FEATURE:
<223> OTHER INFORMATION: Chemically synthesized - Reverse Primer
      pIF-MP-pMAL-SalI Rev

<400> SEQUENCE: 17
gatatgtcga cttagtactg tgtgaaattg gctgtgatgt gctc                                 44

<210> SEQ ID NO 18
<211> LENGTH: 1253
<212> TYPE: DNA
<213> ORGANISM: Homo sapiens

<400> SEQUENCE: 18
atggcctggt ttgccctcta cctcctgagc cttctctggg ctacagctgg gactagtacc                60
cagacccaga gttcatgctc cgttccctca gcacaggagc ccttggtcaa tggaatacaa              120
gtactcatgg agaactcggt gacttcatca gcctacccaa ccccagcat cctgattgcc               180 atgaatctgg ccggagccta caacttgaag gcccagaagc tcctgactta ccagctcatg              240
tccagcgaca caacgatct aaccattggg cacctcggcc tcaccatcat ggccctcacc               300
tcctcctgcc gagaccctgg ggataaagta tccattctac aaagacaaat ggagaactgg              360
gcaccttcca gccccaacgc tgaagcatca gccttctatg gcccagtct agcgatcttg               420 gcactgtgcc agaagaactc tgaggcgacc ttgccgatag ccgtccgctt gccaagacc               480 ctgctggcca actcctctcc cttcaatgta gacacaggag caatggcaac cttggctctg              540
acctgtatgt acaacaagat ccctgtaggt tcagaggaag gttacagatc cctgtttggt              600
caggtactaa aggatattgt ggagaaaatc agcatgaaga tcaaagataa tggcatcatt              660
ggagacatct acagtactgg cctcgccatg caggctctct ctgtaacacc tgagccatct              720
aaaaaggaat ggaactgcaa gaagactacg atatgtgac tcaatgagat taagcagggg               780
aaattccaca accccatgtc cattgctcaa atcctccctt ccctgaaagg caagacatac              840
ctagatgtgc cccaggcact tgtagtcctg atcatgaggt acaaccaact ctacccagca              900
accctggccc tggccccacc tctgcatcta acatcactgt catatacacc ataaataacc              960
agctgagggg ggttgagctg ctcttcaacg agaccatcaa tgttagtgtg aaaagtgggt             1020
cagtgttact tgttgtccta gaggaagcac agcgcaaaaa tcctatgttc aaatttgaaa             1080
ccacaatgac atcttggggc cttgtcgtct cttctatcaa caatatcgcg gaaaatgtta             1140
atcacaagac atactggcag tttcttagtg gtgtaacacc tttgaatgaa ggggttgctg             1200
actacatacc cttcaaccac gagcacatca cagccaattt cacacagtac taa                   1253

<210> SEQ ID NO 19
<211> LENGTH: 1254
<212> TYPE: DNA
<213> ORGANISM: Mouse

<400> SEQUENCE: 19
atggcttggc ttaccctcta cctcctaagt gttctctggg ctgtggcagg aaccagcacc               60

```
cgtgcccaga gctcttgctc tgtgccccca gatcagcaac cctgggtcga tggcctacaa    120
gcgctcatgg agaactcggt gactgactca gacttcccaa accccagcat cctgattgcc    180
atgaacctgg ccggcgccta acgtggag gcccagaaac tcctgactta ccagctcatg    240
gccagtgaca gtgcaaacct gacaagtggg cagcttgccc tcaccgttat ggctctcacg    300
tcctcctgca gagaccctgg aagtaaagtg tccactctac tgaagaaaat ggagaactgg    360
tcaccttcaa gcccgggtgc tgaatcctcg gccttctatg gcctggtttt ggcgatcctc    420
gcactgtgcc agaagagttc agaggcgacc ttacccatcg cagtggcctt cgctaagacc    480
ctgatgatgg aaccctctcc cttcaatgtg gacacaggag cagtggcaac cttggccctg    540
acctgtatgt acaacaagat tcctgtgggt tctcaagaaa actacagaga cctgtttggt    600
caggcactga aggctattgt ggagaagatc agcttaagga tcaaagctga tggcatcatc    660
ggagacatct acagcactgg ccttgccatg caggctctct ccgtgacacc tgagcaacct    720
accaagaagt gggactgtga aagactatg catacaatac tcaacgagat taagcaaggg    780
aaattccaaa ccccatgtc cattgcccaa attctccctt ccttgaaagg caagacttac    840
ctagatgtgc cccaagtaac atgtggtcct gatcatgaag tgccaccaac tttaactgac    900
tatcctaccc cggtccccac ttcagtatct aacattaccg tcatatatac cataaacaac    960
cagctgagag gggttgatcc gcttttcaat gtgaccatcg aggttagtgt gaaaagtgga    1020
tctgtgctac ttgctgtcct ggaagaagca cagcgcaaaa actccatgtt caaatttgaa    1080
accaccatga catcctgggg ccttattgtc tcttctatca acaatatcgc tgagaatgtt    1140
aatcacaaga catactggga gtttcttagt ggcaaaacgc ctttggatga aggggttgct    1200
tactatatcc ccttcaatca tgagcacatc acagccaact tcacccaata ctga          1254
```

<210> SEQ ID NO 20
<211> LENGTH: 1254
<212> TYPE: DNA
<213> ORGANISM: Rat

<400> SEQUENCE: 20

```
atggcctggc tttccttcta cctcctaaat gttctctggg ctgtggcagg aaccagtacc     60
agagcccagc gctcttgctc tgtccccca gatcagcagc cctgggtcaa tggcctacaa    120
ttgctcatgg aaaactcagt aactgagtca gacctcccaa accccagcat cctgattgcc    180
atgaacctgg ccagcaccta caacctggag gcccagaagc tcctgactta ccagctcatg    240
gccagtgaca gtgcagacct gacaaatggg cagctcgccc tcaccattat ggctctcacc    300
tcctcctgcc gagaccctgg aagtaaagtg tccattctac aaaagaatat ggagagctgg    360
acaccttcaa acctgggtgc tgaatcctca tccttctatg gcctgctct ggcgatcctt    420 gcactgtgcc agaagaactc agaggcaacc ttacccatcg cggtgcgctt cgctaagacc    480
ctcatgatgg aatcctctcc cttcagtgtg gacacaggag cagtggcaac cttggccctg    540
acatgcatgt acaacaggat tcctgtgggt tctcaggaaa actacagaga cctgtttggt    600
caggcactga aggttattgt ggataatatc agcttgagga tcaaagctga tggtattatt    660
ggagacatct acagcactgg ccttgccatg caggctctct ctgtgacacc tgagcaacct    720
accaaagagt gggactgtga aagactatg tatacgatac tcaaggagat taagcagggg    780
aaattccaga accccatgtc cattgccag attctccctt ccttgaaagg caagacttac    840
ctagatgtgc cccaagtaac gtgtggccct gatcatgaag tgccaccaac tttaactgac    900
tatcctaccc cggtccccac ttcaatatct aatatcacag tcatatacac cataaacaac    960
```

```
cagctgaggg gggttgatct gcttttcaat gtgaccatcg aggttagtgt gaaaagtgga     1020
tctgtgctcc ttgctgtcct ggaagaagcg cagcgcagaa accacatgtt caaatttgaa     1080
accacaatga catcctgggg ccttattgtc tcttctatca acaatatcgc tgagaatgtt     1140
aagcacaaga cctatttggga gttccttagt ggcaaaacgc ctttgggtga aggggttgca     1200
tactatattc ccttcaacta cgagcacatc acagccaact tcacccaata ctga           1254

<210> SEQ ID NO 21
<211> LENGTH: 1234
<212> TYPE: DNA
<213> ORGANISM: Porcine

<400> SEQUENCE: 21
cctctacctc ctgagccttc tctgggctgt ggccggaacc agcacccaga cccgaagctc       60
atgctctgtt ccctctgcag agcagccctt ggttaatggc atccaggtgc tcatggagca      120
gtccgtgacc agctcggcct cccaaaccc cagcatcctg attgccatga acctggccgg       180
agcctacaac acagaggccc aggagctcct gacttacaag ctcatggcta ccaacacctc      240
cgacctgacc acaggtcagc tcgccctcac catcatggca ctcacctcct cctgccgaga      300
ccctgggaac agaatagcca ttctacaggg gcaaatggag aactgggcac ctccaagcct      360
tgatacccat gcttcaacct tctacgagcc aagtctgggg atcctgacgc tgtgccagaa      420
taacccggag aagaccttac cgctagcagc ccgttttgcc aagaccctgc tggccaattc      480
ctctcccttc aacatggaca caggagcaat ggcaaccttg ccctgacct gtatgtacaa       540 caagatcccc gtaggctcag aggaagggta cagagccctg ttcagtcagg tactgaggaa      600
tactgtggag aatatcagca tgaggatcca agacaacgga tcattggaa acatctatag       660 cactggcctc gccatgcagg ctctctctgt gacacctgag caacctaaca aggagtggga      720
ctgccagaag accatggata ctgtacttac tgagattaag gaggggaaat tccacaaccc      780
catggccatt gcccaaatcc tcccttccct gaaaggcaag acctatctag atgtgcccca      840
tgtgtcttgc agccctggtc atgaggtgcc accaactcta cccaaccacc ccagccctgt      900 tcccaccccca gcacccaaca tcaccgtcat atacaccata ataaccagc tgaggggcgt      960 ggagctgctc ttcaatgaaa ccatcagtgt tagtgtgaaa agaggatccg tgctacttat     1020
tgtcctggag gaggcacagc gcaaaaaccc caagttcaaa tttgaaacga caatgacgtc     1080
ctggggaccg gtggtctctt ctattaacaa tatcgctgaa aatgtcaacc acaggacgta     1140
ctggcagttt ctgagtggcc aaacgcccctt aaacgaagga gttgcggact atataccctt     1200
caaccacgag cacatcacag ccaatttcac acag                                 1234

<210> SEQ ID NO 22
<211> LENGTH: 1254
<212> TYPE: DNA
<213> ORGANISM: Artificial sequence
<220> FEATURE:
<223> OTHER INFORMATION: Chemically synthesized - consensus sequence
<220> FEATURE:
<221> NAME/KEY: misc_feature
<222> LOCATION: (13)..(13)
<223> OTHER INFORMATION: n=a, t, c or g
<220> FEATURE:
<221> NAME/KEY: misc_feature
<222> LOCATION: (205)..(205)
<223> OTHER INFORMATION: n=a, t, c or g
<220> FEATURE:
<221> NAME/KEY: misc_feature
<222> LOCATION: (266)..(266)
```

<223> OTHER INFORMATION: n=a, t, c or g

<400> SEQUENCE: 22

```
atggcctggc ttnccctcta cctcctgagt gttctctggg ctgtggcagg aaccagtacc      60
cgggcccaga gctcttgctc tgttccctca gctcagcagc ccttggtcaa tggcctacaa     120
gtgctcatgg agaactcggt gactgactca gccttcccaa accccagcat cctgattgcc     180
atgaacctgg ccggcgccta caacntggag cccagaagc tcctgactta ccagctcatg     240
gccagtgaca gtgccgacct gaccantggg cagctcgccc tcaccattat ggctctcacc     300
tcctcctgcc gagaccctgg gagtaaagtg tccattctac agaggcaaat ggagaactgg     360
gcaccttcaa gcctgggtgc tgaatcctca gccttctatg gcctggtct ggcgatcctg     420
gcactgtgcc agaagaactc agaggcgacc ttaccgatcg cagtgcgctt tgctaagacc     480
ctgctggtgg aatcctctcc cttcaatgtg gacacaggag cagtggcaac cttggccctg     540
acctgtatgt acaacaagat tcctgtgggt tctgaggaag gctacagagc cctgtttggt     600
caggtactga aggatattgt ggagaatatc agcttgagga tcaaagctga tggcatcatt     660
ggagacatct acagcactgg ccttgccatg caggctctct ctgtgacacc tgagcaacct     720
accaaggagt gggactgtga aagactatg gatacgatac tcaatgagat taagcagggg     780
aaattccaca ccccatgtc cattgcccaa attctccctt ccttgaaagg caagacttac     840
ctagatgtgc cccaagtaac ttgtggtcct gatcatgagg tgccaccaac tttacctgac     900
tatcctagcc ctgtccccac ttcagtatct aacatcaccg tcatatacac cataaataac     960
cagctgaggg gggttgatct gcttttcaat gtgaccatcg atgttagtgt gaaaagtgga    1020
tctgtgctac ttgttgtcct ggaggaagca cagcgcaaaa accccatgtt caaatttgaa    1080
accacaatga catcctgggg ccttgttgtc tcttctatca caatatcgc tgagaatgtt    1140
aatcacaaga catactggga gtttcttagt ggcaaaacgc ctttggatga agggggttgct    1200
tactatatac ccttcaacca cgagcacatc acagccaatt tcacccagta ctga          1254
```

<210> SEQ ID NO 23
<211> LENGTH: 417
<212> TYPE: PRT
<213> ORGANISM: Homo sapiens

<400> SEQUENCE: 23

```
Met Ala Trp Phe Ala Leu Tyr Leu Leu Ser Leu Leu Trp Ala Thr Ala
1               5                   10                  15

Gly Thr Ser Thr Gln Thr Gln Ser Ser Cys Ser Val Pro Ser Ala Gln
            20                  25                  30

Glu Pro Leu Val Asn Gly Ile Gln Val Leu Met Glu Asn Ser Val Thr
        35                  40                  45

Ser Ser Ala Tyr Pro Asn Pro Ser Ile Leu Ile Ala Met Asn Leu Ala
    50                  55                  60

Gly Ala Tyr Asn Leu Lys Ala Gln Lys Leu Leu Thr Tyr Gln Leu Met
65                  70                  75                  80

Ser Ser Asp Asn Asn Asp Leu Thr Ile Gly His Leu Gly Leu Thr Ile
                85                  90                  95

Met Ala Leu Thr Ser Ser Cys Arg Asp Pro Gly Asp Lys Val Ser Ile
            100                 105                 110

Leu Gln Arg Gln Met Glu Asn Trp Ala Pro Ser Ser Pro Asn Ala Glu
        115                 120                 125

Ala Ser Ala Phe Tyr Gly Pro Ser Leu Ala Ile Leu Ala Leu Cys Gln
```

```
                130                 135                 140
Lys Asn Ser Glu Ala Thr Leu Pro Ile Ala Val Arg Phe Ala Lys Thr
145                 150                 155                 160

Leu Leu Ala Asn Ser Ser Pro Phe Asn Val Asp Thr Gly Ala Met Ala
                165                 170                 175

Thr Leu Ala Leu Thr Cys Met Tyr Asn Lys Ile Pro Val Gly Ser Glu
            180                 185                 190

Glu Gly Tyr Arg Ser Leu Phe Gly Gln Val Leu Lys Asp Ile Val Glu
        195                 200                 205

Lys Ile Ser Met Lys Ile Lys Asp Asn Gly Ile Gly Asp Ile Tyr
    210                 215                 220

Ser Thr Gly Leu Ala Met Gln Ala Leu Ser Val Thr Pro Glu Pro Ser
225                 230                 235                 240

Lys Lys Glu Trp Asn Cys Lys Lys Thr Thr Asp Met Ile Leu Asn Glu
                245                 250                 255

Ile Lys Gln Gly Lys Phe His Asn Pro Met Ser Ile Ala Gln Ile Leu
            260                 265                 270

Pro Ser Leu Lys Gly Lys Thr Tyr Leu Asp Val Pro Gln Val Thr Cys
        275                 280                 285

Ser Pro Asp His Glu Val Gln Pro Thr Leu Pro Ser Asn Pro Gly Pro
    290                 295                 300

Gly Pro Thr Ser Ala Ser Asn Ile Thr Val Ile Tyr Thr Ile Asn Asn
305                 310                 315                 320

Gln Leu Arg Gly Val Glu Leu Leu Phe Asn Glu Thr Ile Asn Val Ser
                325                 330                 335

Val Lys Ser Gly Ser Val Leu Leu Val Val Leu Glu Glu Ala Gln Arg
            340                 345                 350

Lys Asn Pro Met Phe Lys Phe Glu Thr Thr Met Thr Ser Trp Gly Leu
        355                 360                 365

Val Val Ser Ser Ile Asn Asn Ile Ala Glu Asn Val Asn His Lys Thr
    370                 375                 380

Tyr Trp Gln Phe Leu Ser Gly Val Thr Pro Leu Asn Glu Gly Val Ala
385                 390                 395                 400

Asp Tyr Ile Pro Phe Asn His Glu His Ile Thr Ala Asn Phe Thr Gln
                405                 410                 415

Tyr

<210> SEQ ID NO 24
<211> LENGTH: 417
<212> TYPE: PRT
<213> ORGANISM: Mouse

<400> SEQUENCE: 24

Met Ala Trp Leu Thr Leu Tyr Leu Leu Ser Val Leu Trp Ala Val Ala
1               5                   10                  15

Gly Thr Ser Thr Arg Ala Gln Ser Ser Cys Ser Val Pro Pro Asp Gln
            20                  25                  30

Gln Pro Trp Val Asp Gly Leu Gln Ala Leu Met Glu Asn Ser Val Thr
        35                  40                  45

Asp Ser Asp Phe Pro Asn Pro Ser Ile Leu Ile Ala Met Asn Leu Ala
    50                  55                  60

Gly Ala Tyr Asn Val Glu Ala Gln Lys Leu Leu Thr Tyr Gln Leu Met
65                  70                  75                  80

Ala Ser Asp Ser Ala Asn Leu Thr Ser Gly Gln Leu Ala Leu Thr Val
```

```
                    85                  90                  95
Met Ala Leu Thr Ser Ser Cys Arg Asp Pro Gly Ser Lys Val Ser Thr
                100                 105                 110

Leu Leu Lys Lys Met Glu Asn Trp Ser Pro Ser Pro Gly Ala Glu
            115                 120                 125

Ser Ser Ala Phe Tyr Gly Pro Gly Leu Ala Ile Leu Ala Leu Cys Gln
        130                 135                 140

Lys Ser Ser Glu Ala Thr Leu Pro Ile Ala Val Ala Phe Ala Lys Thr
145                 150                 155                 160

Leu Met Met Glu Pro Ser Pro Phe Asn Val Asp Thr Gly Ala Val Ala
                165                 170                 175

Thr Leu Ala Leu Thr Cys Met Tyr Asn Lys Ile Pro Val Gly Ser Gln
                180                 185                 190

Glu Asn Tyr Arg Asp Leu Phe Gly Gln Ala Leu Lys Ala Ile Val Glu
            195                 200                 205

Lys Ile Ser Leu Arg Ile Lys Ala Asp Gly Ile Ile Gly Asp Ile Tyr
        210                 215                 220

Ser Thr Gly Leu Ala Met Gln Ala Leu Ser Val Thr Pro Glu Gln Pro
225                 230                 235                 240

Thr Lys Lys Trp Asp Cys Glu Lys Thr Met His Thr Ile Leu Asn Glu
                245                 250                 255

Ile Lys Gln Gly Lys Phe Gln Asn Pro Met Ser Ile Ala Gln Ile Leu
            260                 265                 270

Pro Ser Leu Lys Gly Lys Thr Tyr Leu Asp Val Pro Gln Val Thr Cys
        275                 280                 285

Gly Pro Asp His Glu Val Pro Pro Thr Leu Thr Asp Tyr Pro Thr Pro
        290                 295                 300

Val Pro Thr Ser Val Ser Asn Ile Thr Val Ile Tyr Thr Ile Asn Asn
305                 310                 315                 320

Gln Leu Arg Gly Val Asp Pro Leu Phe Asn Val Thr Ile Glu Val Ser
                325                 330                 335

Val Lys Ser Gly Ser Val Leu Leu Ala Val Leu Glu Glu Ala Gln Arg
            340                 345                 350

Lys Asn Ser Met Phe Lys Phe Glu Thr Thr Met Thr Ser Trp Gly Leu
        355                 360                 365

Ile Val Ser Ser Ile Asn Asn Ile Ala Glu Asn Val Asn His Lys Thr
        370                 375                 380

Tyr Trp Glu Phe Leu Ser Gly Lys Thr Pro Leu Asp Glu Gly Val Ala
385                 390                 395                 400

Tyr Tyr Ile Pro Phe Asn His Glu His Ile Thr Ala Asn Phe Thr Gln
                405                 410                 415

Tyr

<210> SEQ ID NO 25
<211> LENGTH: 421
<212> TYPE: PRT
<213> ORGANISM: Rat

<400> SEQUENCE: 25

Met Trp Lys Gly Met Ala Trp Leu Ser Phe Tyr Leu Leu Asn Val Leu
1               5                   10                  15

Trp Ala Val Ala Gly Thr Ser Thr Arg Ala Gln Arg Ser Cys Ser Val
            20                  25                  30

Pro Pro Asp Gln Gln Pro Trp Val Asn Gly Leu Gln Leu Leu Met Glu
```

-continued

```
                35                  40                  45
Asn Ser Val Thr Glu Ser Asp Leu Pro Asn Pro Ser Ile Leu Ile Ala
 50                  55                  60

Met Asn Leu Ala Ser Thr Tyr Asn Leu Glu Ala Gln Lys Leu Leu Thr
 65                  70                  75                  80

Tyr Gln Leu Met Ala Ser Asp Ser Ala Asp Leu Thr Asn Gly Gln Leu
                 85                  90                  95

Ala Leu Thr Ile Met Ala Leu Thr Ser Ser Cys Arg Asp Pro Gly Ser
                100                 105                 110

Lys Val Ser Ile Leu Gln Lys Asn Met Glu Ser Trp Thr Pro Ser Asn
                115                 120                 125

Leu Gly Ala Glu Ser Ser Phe Tyr Gly Pro Ala Leu Ala Ile Leu
                130                 135                 140

Ala Leu Cys Gln Lys Asn Ser Glu Ala Thr Leu Pro Ile Ala Val Arg
145                 150                 155                 160

Phe Ala Lys Thr Leu Met Met Glu Ser Ser Pro Phe Ser Val Asp Thr
                165                 170                 175

Gly Ala Val Ala Thr Leu Ala Leu Thr Cys Met Tyr Asn Arg Ile Pro
                180                 185                 190

Val Gly Ser Gln Glu Asn Tyr Arg Asp Leu Phe Gly Gln Ala Leu Lys
                195                 200                 205

Val Ile Val Asp Asn Ile Ser Leu Arg Ile Lys Ala Asp Gly Ile Ile
                210                 215                 220

Gly Asp Ile Tyr Ser Thr Gly Leu Ala Met Gln Ala Leu Ser Val Thr
225                 230                 235                 240

Pro Glu Gln Pro Thr Lys Glu Trp Asp Cys Glu Lys Thr Met Tyr Thr
                245                 250                 255

Ile Leu Lys Glu Ile Lys Gln Gly Lys Phe Gln Asn Pro Met Ser Ile
                260                 265                 270

Ala Gln Ile Leu Pro Ser Leu Lys Gly Lys Thr Tyr Leu Asp Val Pro
                275                 280                 285

Gln Val Thr Cys Gly Pro Asp His Glu Val Pro Pro Thr Leu Thr Asp
                290                 295                 300

Tyr Pro Thr Pro Val Pro Thr Ser Ile Ser Asn Ile Thr Val Ile Tyr
305                 310                 315                 320

Thr Ile Asn Asn Gln Leu Arg Gly Val Asp Leu Leu Phe Asn Val Thr
                325                 330                 335

Ile Glu Val Ser Val Lys Ser Gly Ser Val Leu Leu Ala Val Leu Glu
                340                 345                 350

Glu Ala Gln Arg Arg Asn His Met Phe Lys Phe Glu Thr Thr Met Thr
                355                 360                 365

Ser Trp Gly Leu Ile Val Ser Ser Ile Asn Asn Ile Ala Glu Asn Val
370                 375                 380

Lys His Lys Thr Tyr Trp Glu Phe Leu Ser Lys Thr Pro Leu Gly
385                 390                 395                 400

Glu Gly Val Ala Tyr Tyr Ile Pro Phe Asn Tyr Glu His Ile Thr Ala
                405                 410                 415

Asn Phe Thr Gln Tyr
                420

<210> SEQ ID NO 26
<211> LENGTH: 411
<212> TYPE: PRT
<213> ORGANISM: porcine
```

<400> SEQUENCE: 26

```
Leu Tyr Leu Leu Ser Leu Leu Trp Ala Val Ala Gly Thr Ser Thr Gln
1               5                   10                  15

Thr Arg Ser Ser Cys Ser Val Pro Ser Ala Glu Gln Pro Leu Val Asn
            20                  25                  30

Gly Ile Gln Val Leu Met Glu Gln Ser Val Thr Ser Ser Ala Phe Pro
        35                  40                  45

Asn Pro Ser Ile Leu Ile Ala Met Asn Leu Ala Gly Ala Tyr Asn Thr
    50                  55                  60

Glu Ala Gln Glu Leu Leu Thr Tyr Lys Leu Met Ala Thr Asn Thr Ser
65                  70                  75                  80

Asp Leu Thr Thr Gly Gln Leu Ala Leu Thr Ile Met Ala Leu Thr Ser
                85                  90                  95

Ser Cys Arg Asp Pro Gly Asn Arg Ile Ala Ile Leu Gln Gly Gln Met
            100                 105                 110

Glu Asn Trp Ala Pro Pro Ser Leu Asp Thr His Ala Ser Thr Phe Tyr
        115                 120                 125

Glu Pro Ser Leu Gly Ile Leu Thr Leu Cys Gln Asn Asn Pro Glu Lys
    130                 135                 140

Thr Leu Pro Leu Ala Ala Arg Phe Ala Lys Thr Leu Leu Ala Asn Ser
145                 150                 155                 160

Ser Pro Phe Asn Met Asp Thr Gly Ala Met Ala Thr Leu Ala Leu Thr
                165                 170                 175

Cys Met Tyr Asn Lys Ile Pro Val Gly Ser Glu Gly Tyr Arg Ala
            180                 185                 190

Leu Phe Ser Gln Val Leu Arg Asn Thr Val Glu Asn Ile Ser Met Arg
        195                 200                 205

Ile Gln Asp Asn Gly Ile Ile Gly Asn Ile Tyr Ser Thr Gly Leu Ala
    210                 215                 220

Met Gln Ala Leu Ser Val Thr Pro Glu Gln Pro Asn Lys Glu Trp Asp
225                 230                 235                 240

Cys Gln Lys Thr Met Asp Thr Val Leu Thr Glu Ile Lys Glu Gly Lys
                245                 250                 255

Phe His Asn Pro Met Ala Ile Ala Gln Ile Leu Pro Ser Leu Lys Gly
            260                 265                 270

Lys Thr Tyr Leu Asp Val Pro His Val Ser Cys Ser Pro Gly His Glu
        275                 280                 285

Val Pro Pro Thr Leu Pro Asn His Pro Ser Pro Val Pro Thr Pro Ala
    290                 295                 300

Pro Asn Ile Thr Val Ile Tyr Thr Ile Asn Asn Gln Leu Arg Gly Val
305                 310                 315                 320

Glu Leu Leu Phe Asn Glu Thr Ile Ser Val Ser Val Lys Arg Gly Ser
                325                 330                 335

Val Leu Leu Ile Val Leu Glu Glu Ala Gln Arg Lys Asn Pro Lys Phe
            340                 345                 350

Lys Phe Glu Thr Thr Met Thr Ser Trp Gly Pro Val Val Ser Ser Ile
        355                 360                 365

Asn Asn Ile Ala Glu Asn Val Asn His Arg Thr Tyr Trp Gln Phe Leu
    370                 375                 380

Ser Gly Gln Thr Pro Leu Asn Glu Gly Val Ala Asp Tyr Ile Pro Phe
385                 390                 395                 400

Asn His Glu His Ile Thr Ala Asn Phe Thr Gln
```

-continued

```
                        405                 410

<210> SEQ ID NO 27
<211> LENGTH: 417
<212> TYPE: PRT
<213> ORGANISM: Artificial sequence
<220> FEATURE:
<223> OTHER INFORMATION: Chemically synthesized - consensus sequence
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (89)..(89)
<223> OTHER INFORMATION: Xaa can be any naturally occurring amino acid
<220> FEATURE:
<221> NAME/KEY: misc_feature
<222> LOCATION: (205)..(205)
<223> OTHER INFORMATION: Xaa can be any naturally occurring amino acid

<400> SEQUENCE: 27

Met Ala Trp Leu Xaa Leu Tyr Leu Leu Ser Val Leu Trp Ala Val Ala
1               5                   10                  15

Gly Thr Ser Thr Gln Ala Gln Ser Ser Cys Ser Val Pro Ser Ala Gln
            20                  25                  30

Gln Pro Leu Val Asn Gly Leu Gln Val Leu Met Glu Asn Ser Val Thr
        35                  40                  45

Ser Ser Ala Phe Pro Asn Pro Ser Ile Leu Ile Ala Met Asn Leu Ala
    50                  55                  60

Gly Ala Tyr Asn Leu Glu Ala Gln Lys Leu Leu Thr Tyr Gln Leu Met
65                  70                  75                  80

Ala Ser Asp Ser Ala Asp Leu Thr Xaa Gly Gln Leu Ala Leu Thr Ile
                85                  90                  95

Met Ala Leu Thr Ser Ser Cys Arg Asp Pro Gly Ser Lys Val Ser Ile
            100                 105                 110

Leu Gln Lys Gln Met Glu Asn Trp Ala Pro Ser Ser Leu Gly Ala Glu
        115                 120                 125

Ala Ser Ala Phe Tyr Gly Pro Ser Leu Ala Ile Leu Ala Leu Cys Gln
    130                 135                 140

Lys Asn Ser Glu Ala Thr Leu Pro Ile Ala Val Arg Phe Ala Lys Thr
145                 150                 155                 160

Leu Leu Ala Glu Ser Ser Pro Phe Asn Val Asp Thr Gly Ala Val Ala
                165                 170                 175

Thr Leu Ala Leu Thr Cys Met Tyr Asn Lys Ile Pro Val Gly Ser Glu
            180                 185                 190

Glu Gly Tyr Arg Asp Leu Phe Gly Gln Ala Leu Lys Xaa Ile Val Glu
        195                 200                 205

Asn Ile Ser Leu Arg Ile Lys Ala Asp Gly Ile Gly Asp Ile Tyr
    210                 215                 220

Ser Thr Gly Leu Ala Met Gln Ala Leu Ser Val Thr Pro Glu Gln Pro
225                 230                 235                 240

Thr Lys Glu Trp Asp Cys Glu Lys Thr Met Asp Thr Ile Leu Asn Glu
                245                 250                 255

Ile Lys Gln Gly Lys Phe Gln Asn Pro Met Ser Ile Ala Gln Ile Leu
            260                 265                 270

Pro Ser Leu Lys Gly Lys Thr Tyr Leu Asp Val Pro Gln Val Thr Cys
        275                 280                 285

Gly Pro Asp His Glu Val Pro Pro Thr Leu Thr Asp Tyr Pro Thr Pro
```

-continued

```
            290                 295                 300
Val Pro Thr Ser Ala Ser Asn Ile Thr Val Ile Tyr Thr Ile Asn Asn
305                 310                 315                 320

Gln Leu Arg Gly Val Asp Leu Leu Phe Asn Val Thr Ile Glu Val Ser
                325                 330                 335

Val Lys Ser Gly Ser Val Leu Leu Ala Val Leu Glu Glu Ala Gln Arg
                340                 345                 350

Lys Asn Pro Met Phe Lys Phe Glu Thr Thr Met Thr Ser Trp Gly Leu
            355                 360                 365

Val Val Ser Ser Ile Asn Asn Ile Ala Glu Asn Val Asn His Lys Thr
370                 375                 380

Tyr Trp Glu Phe Leu Ser Gly Lys Thr Pro Leu Asn Glu Gly Val Ala
385                 390                 395                 400

Asp Tyr Ile Pro Phe Asn His Glu His Ile Thr Ala Asn Phe Thr Gln
                405                 410                 415

Tyr
```